(12) United States Patent
Yuan et al.

(10) Patent No.: US 12,702,555 B2
(45) Date of Patent: Aug. 11, 2026

(54) DEVICES, SYSTEMS, AND METHODS FOR TREATING CONDITIONS OF THE HEART

(71) Applicant: ConKay Medical Systems, Inc., Pleasanton, CA (US)

(72) Inventors: Shih-hsiung Albert Yuan, Pleasanton, CA (US); Ashley C. Pittner, Tucson, AZ (US); Jordan M. Skaro, San Jose, CA (US)

(73) Assignee: ConKay Medical Systems, Inc., Pleasanton, CA (US)

( * ) Notice: Subject to any disclaimer, the term of this patent is extended or adjusted under 35 U.S.C. 154(b) by 643 days.

(21) Appl. No.: 18/298,283

(22) Filed: Apr. 10, 2023

(65) Prior Publication Data

US 2024/0008985 A1 Jan. 11, 2024

Related U.S. Application Data

(63) Continuation of application No. PCT/US2022/016674, filed on Feb. 16, 2022.

(Continued)

(51) Int. Cl.

*A61F 2/24* (2006.01)
*A61B 17/00* (2006.01)

(52) U.S. Cl.

CPC ...... *A61F 2/2466* (2013.01); *A61B 17/00234* (2013.01); *A61F 2/2427* (2013.01); *A61B 2017/00243* (2013.01); *A61F 2220/0016* (2013.01); *A61F 2220/0075* (2013.01); *A61F 2250/001* (2013.01)

(58) Field of Classification Search

None

See application file for complete search history.

(56) References Cited

U.S. PATENT DOCUMENTS 10,575,952 B2 * 3/2020 Alon .................... A61F 2/0077
2011/0166649 A1 * 7/2011 Gross .................... A61F 2/2466
623/2.36

(Continued)

FOREIGN PATENT DOCUMENTS

CN 114901197 B * 1/2026 ............ A61B 46/10
JP 2016512726 A 5/2016

(Continued)

OTHER PUBLICATIONS

International Search Report and Written Opinion dated May 31, 2022; International Application No. PCT/ JS2022/016674; 13 pages.

*Primary Examiner* — Tan-Uyen T Ho
(74) *Attorney, Agent, or Firm* — FORTEM IP LLP

(57) ABSTRACT

Devices for treating a native valve annulus are disclosed herein. In some examples, the present technology includes a device comprising a plurality of arms configured to move independently of one another and a coupler coupled to the arms and configured to move relative to the arms. The device can further include a plurality of anchors, each carried by the distal portion of one of the arms and configured to engage tissue at or proximate the annulus. When the device is in a deployed configuration such that the arms extend axially and radially away from the coupler, movement of the coupler relative to the arms may decrease a circumferential distance between at least some of the anchors.

20 Claims, 35 Drawing Sheets

Related U.S. Application Data

(60) Provisional application No. 63/263,354, filed on Nov. 1, 2021, provisional application No. 63/223,965, filed on Jul. 20, 2021, provisional application No. 63/200,455, filed on Mar. 8, 2021, provisional application No. 63/150,014, filed on Feb. 16, 2021.

(56) References Cited

U.S. PATENT DOCUMENTS

| | | | | |
|---|---|---|---|---|
| 2012/0083806 | A1* | 4/2012 | Goertzen | A61B 17/0401 606/151 |
| 2018/0214270 | A1 | 8/2018 | Subramanian et al. | |
| 2019/0117397 | A1 | 4/2019 | Alon | |
| 2021/0022850 | A1 | 1/2021 | Basude et al. | |
| 2021/0161664 | A1* | 6/2021 | Krumpelmann | A61F 2/2445 |

FOREIGN PATENT DOCUMENTS

| | | | |
|---|---|---|---|
| JP | 2016520398 | A | 7/2016 |
| WO | 2017136596 | A1 | 8/2017 |
| WO | 2018148584 | A1 | 8/2018 |
| WO | 2020206012 | A1 | 10/2020 |
| WO | 2020236757 | A1 | 11/2020 |
| WO | 2022178042 | A1 | 8/2022 |

* cited by examiner 904
902b
904
902
902a
909
L
906
902
904
912
902
2603
904

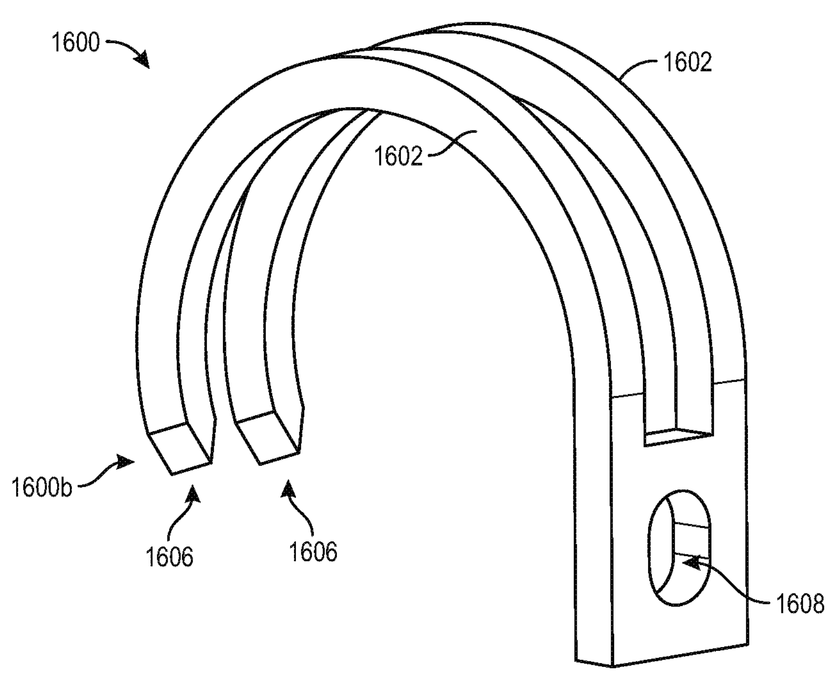
FIG. 33
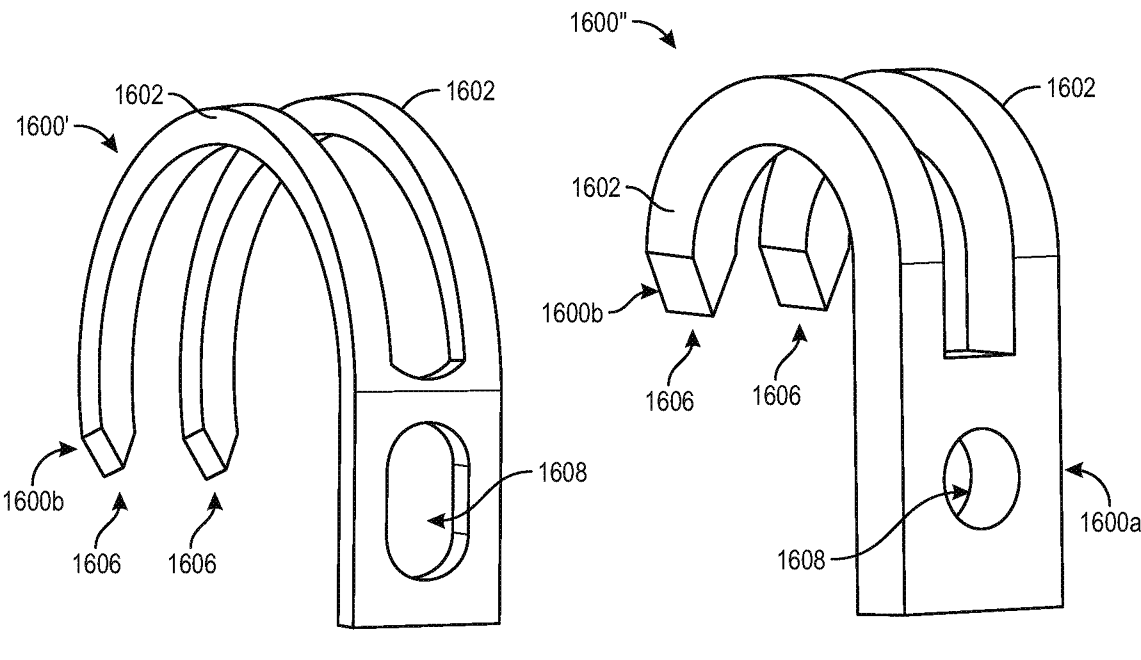
FIG. 34
FIG. 35

DEVICES, SYSTEMS, AND METHODS FOR TREATING CONDITIONS OF THE HEART

CROSS-REFERENCE TO RELATED APPLICATION(S)

The present application is a continuation of International Patent Application No. PCT/US2022/016674, filed Feb. 16, 2022, which claims the benefit of priority to U.S. Provisional Application No. 63/263,354, filed Nov. 1, 2021, U.S. Provisional Application No. 63/223,965, filed Jul. 20, 2021, U.S. Provisional Application No. 63/200,455, filed Mar. 8, 2021, and U.S. Provisional Application No. 63/150,014, filed Feb. 16, 2021, each of which is incorporated by reference herein in its entirety.

TECHNICAL FIELD

The present technology relates to devices, systems, and methods for treating conditions of the heart.

BACKGROUND

Valvular regurgitation (VR) is a common valvular heart disease (VHD) where the failure of one of the heart's valves to close tightly allows blood to flow backward through the valve. Patients can have shortness of breath, fatigue, chest pain, a fluttering heartbeat, and sometimes death. About 15% of people over 75 years old have valvular heart disease, affecting at least 2.5% of the U.S. Population and more than 100 million people globally. Today, surgical mitral valve repair is a robust and effective procedure to correct mitral regurgitation, with years of clinical experience and validated evidence. However, surgical mitral intervention in high-risk patients is still a challenging procedure, with 30-day mortality approaching 3.1%. The mortality rate is even higher in patients with functional mitral regurgitation, where a concomitant impairment of the left ventricular ejection fraction is often observed. Treatment of tricuspid regurgitation also faces serious obstacles. Current products have issues with visual imaging, pacemaker lead interactions, and are also not capable of treating patients with larger valves. For these reasons, emerging low risk percutaneous strategies are needed to treat VHD in both degenerative and functional anatomies, and to minimize the potential complications associated with open-heart surgery.

SUMMARY

The subject technology is illustrated, for example, according to various aspects described below, including with reference to FIGS. 1-39. Various examples of aspects of the subject technology are described as numbered clauses (1, 2, 3, etc.) for convenience. These are provided as examples and do not limit the subject technology.

1. A device for treating a native valve annulus, the device comprising:
   a plurality of arms, each having a proximal portion and a distal portion, wherein the arms are configured to move independently of one another;
   a coupler coupled to the arms and configured to move relative to the arms; and
   a plurality of anchors, each carried by the distal portion of one of the arms and configured to engage tissue at or proximate the annulus,
   wherein, when the device is in a deployed configuration such that the arms extend axially and radially away from the coupler, movement of the coupler relative to the arms decreases a circumferential distance between at least some of the anchors.

2. The device of Clause 1, wherein the valve annulus is a cardiac valve annulus, and wherein the device is configured to be delivered proximate to and above the annulus such that the anchors are implanted in the annular cardiac tissue just above the plane of the valve orifice.
3. The device of Clause 1 or Clause 2, wherein the coupler is configured to translate and/or rotate relative to the arms.
4. The device of any one of Clauses 1 to 3, wherein the arms are configured to translate and/or rotate independently of one another.
5. The device of any one of Clauses 1 to 4, wherein each of the arms includes one or more locking elements, and wherein movement of the coupler relative to the arms causes the coupler to engage at least some of the locking elements on at least some of the arms, thereby fixing an axial position of each of the arms relative to the other arms and/or the coupler.
6. The device of any one of Clauses 1 to 5, wherein, when the arms are in a deployed configuration, movement of the coupler relative to the arms decreases an angle between adjacent arms.
7. The device of any one of Clauses 1 to 6, wherein each of the anchors is detachably coupled to one of the arms such that, upon completion of treatment, the coupler and arms are removed from the patient while the anchors are left implanted at the annulus.
8. The device of any one of Clauses 1 to 7, wherein each of the anchors is attached to a single arm.
9. The device of any one of Clauses 1 to 8, further comprising a suture coupled to the anchors.
10. The device of any one of Clauses 1 to 9, wherein some or all of the arms comprise at least one of a tube, a solid rod, or a ribbon.
11. The device of any one of Clauses 1 to 10, wherein the device is configured to be percutaneously delivered to the annulus.
12. A device for treating a native valve annulus, the device comprising:
   a plurality of arms;
   a coupler coupled to the arms, wherein the coupler is configured to move relative to the arms; and
   a plurality of anchors, each carried by a distal portion of one of the arms and configured to be implanted at or proximate the annulus,
   wherein, when the device is in a deployed configuration movement of the coupler relative to the arms decreases a circumferential distance between at least some of the anchors.
13. A system for treating a native valve annulus, the system comprising:
   a plurality of elongate members, each having a proximal region and a distal region;
   a plurality of arms configured to be positioned at or proximate the annulus, each of the arms having a proximal portion and a distal portion, wherein each of the distal portions are coupled to the distal region of a corresponding elongate member;
   a coupler coupled to the arms and configured to move relative to the arms; and
   a plurality of anchors, each coupled to the distal portion of one of the arms and configured to engage tissue at or proximate the annulus, wherein, when the arms are in a deployed configuration, movement of the coupler relative to the arms decreases an area circumscribed by the anchors.

14. The system of Clause 13, wherein the elongate members are first elongate members and the system further comprises a second elongate member having a proximal region and a distal region, wherein the distal region of the second elongate member is coupled to the coupler such that movement of the second elongate member causes movement of the coupler relative to the arms.
15. The system of Clause 14, wherein the second elongate member is a solid rod.
16. The system of Clause 14, wherein the second elongate member is a flexible tube.
17. The system of Clause 14, wherein the second elongate member is an elongate shaft that surrounds the first elongate members.
18. The system of any one of Clauses 13 to 17, wherein rotation and/or translation of one of the elongate members causes rotation and/or translation of the corresponding arm.
19. The system of any one of Clauses 13 to 18, wherein the coupler is configured to translate and/or rotate relative to the arms.
20. The system of any one of Clauses 13 to 19, wherein each of the anchors is detachably coupled to one of the arms.
21. The system of Clause 20, wherein actuation of one of the elongate members causes the corresponding anchor to detach from the corresponding arm.
22. The system of any one of Clauses 13 to 21, further comprising a suture coupled to the anchors and extending proximally along the elongate members.
23. The system of any one of Clauses 13 to 22, further comprising an imaging element configured to be advanced to a location at or proximate the annulus while the arms are positioned at or proximate the annulus.
24. The system of any one of Clauses 13 to 23, wherein each of the arms includes one or more locking elements, and wherein movement of the coupler relative to the arms causes the coupler to engage at least some of the locking elements on at least some of the arms, thereby fixing an axial position of each of the arms relative to the other arms and/or the coupler.
25. A method for treating a native valve annulus of a patient, the method comprising:
    positioning a device at or proximate the valve annulus in a low-profile delivery configuration, the device comprising a plurality of arms, a coupler coupled to the arms, and a plurality of anchors, each of the anchors coupled to one of the arms;
    causing the device to expand into a deployed configuration in which the arms extend radially away from the coupler;
    engaging tissue at or proximate the annulus with at least some of the anchors; and
    changing a shape of the valve orifice by moving the coupler relative to the arms.
26. The method of Clause 25, wherein changing a shape of the valve orifice includes decreasing an area of the valve orifice.
27. The method of Clause 25 or Clause 26, further comprising substantially fixing a length of a suture coupled to and extending between the anchors after changing a shape of the valve orifice.
28. The method of any one of Clauses 25 to 27, further comprising:
    detaching the anchors from the arms, thereby leaving the anchors implanted at the annulus; and
    removing the arms and the coupler from the patient.
29. The method of any one of Clauses 25 to 28, wherein the valve annulus is a cardiac valve annulus, and wherein the device is deployed proximate to and above the annulus such that the anchors are implanted in the annular cardiac tissue just above the plane of the valve orifice.
30. The method of any one of Clauses 25 to 29, wherein moving the coupler relative to the arms decreases an angle and/or a circumferential distance between a) adjacent arms and/or b) adjacent anchors.
31. The method of any one of Clauses 25 to 30, wherein moving the coupler relative to the arms comprises translating the coupler distally along the arms.
32. The method of any one of Clauses 25 to 31, further comprising rotating and/or translating one or more of the arms independently of one or more of the other arms.
33. The method of any one of Clauses 25 to 32, further comprising rotating the device to engage the tissue with the anchors.
34. The method of any one of Clauses 25 to 33, wherein moving the coupler comprises engaging one or more locking elements on one or more of the arms with the coupler, thereby fixing the arms longitudinally relative to one another and/or the coupler.
35. The method of any one of Clauses 25 to 34, wherein the device is positioned at the valve annulus percutaneously.

BRIEF DESCRIPTION OF THE DRAWINGS

Many aspects of the present disclosure can be better understood with reference to the following drawings. The components in the drawings are not necessarily to scale. Instead, emphasis is placed on illustrating clearly the principles of the present disclosure.

FIGS. 33-35 show different anchors configured in accordance with several embodiments of the present technology.

DETAILED DESCRIPTION

The present technology relates to devices, systems, and methods for treating a structure of the heart, such as a native heart valve. Some embodiments of the present technology, for example, are directed to devices, systems, and methods for reshaping a native valve annulus, such as a native heart valve annulus. Specific details of several embodiments of the technology are described below with reference to FIGS. 1-39.

Figure 1:
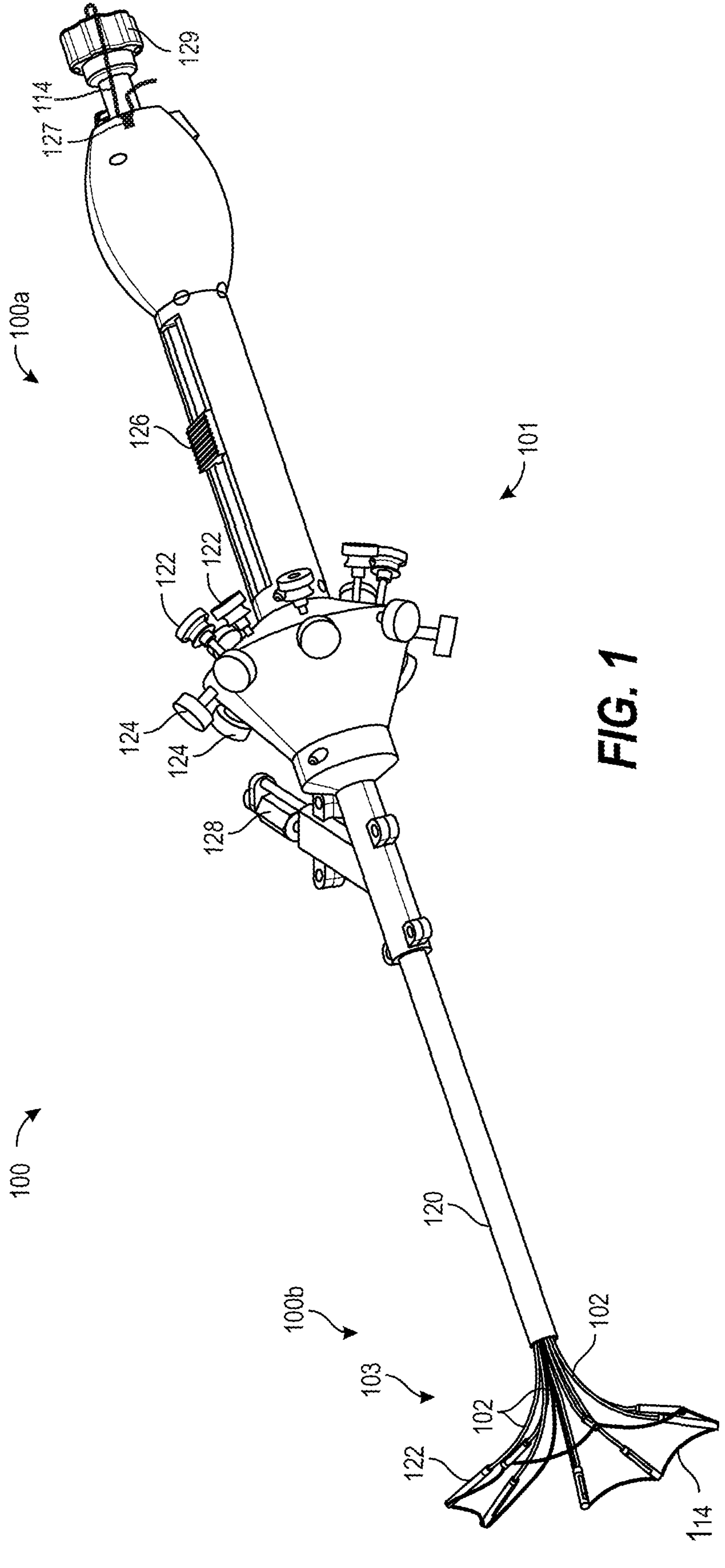
FIG. 1 shows a treatment device configured in accordance with several embodiments of the present technology.

FIG. 1 shows a device 100 for treating a cardiac valve annulus, configured in accordance with several embodiments of the present technology. The device 100 has a proximal portion 100*a* comprising a handle 101 configured to be extracorporeally positioned during treatment and a distal portion 100*b* configured to be percutaneously positioned proximate to, above and/or or within a cardiac valve annulus. The distal portion 100*b* of the device 100 includes a distal assembly 103 that is configured to be manipulated by one or more actuators (e.g., buttons, sliders, knobs, etc.) at the handle 101 to implant a plurality of anchors in the annular cardiac tissue just above and/or within the plane of the valve orifice. The device 100 may further include an elongate shaft 120 extending distally from the handle 101 to the distal portion 100*b* of the device, as well as a coupler 129 for receiving one or more other devices (such as a finishing device, as disclosed herein) and/or a suture 114 therethrough.

Figure 2A:
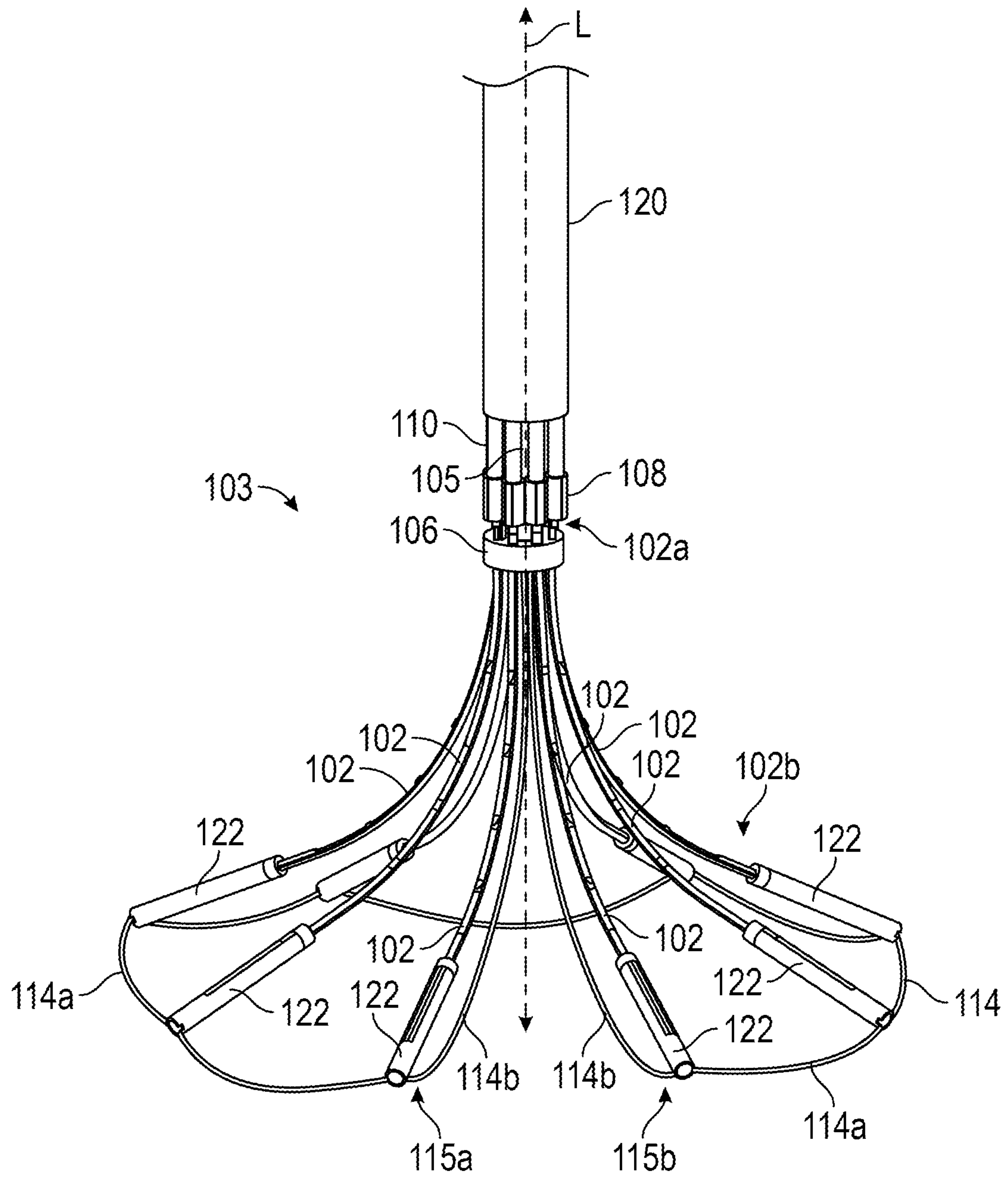
FIGS. 2A and 2B show a distal assembly of the treatment device in first and second positions, respectively, in accordance with several embodiments of the present technology.
Figure 2B:
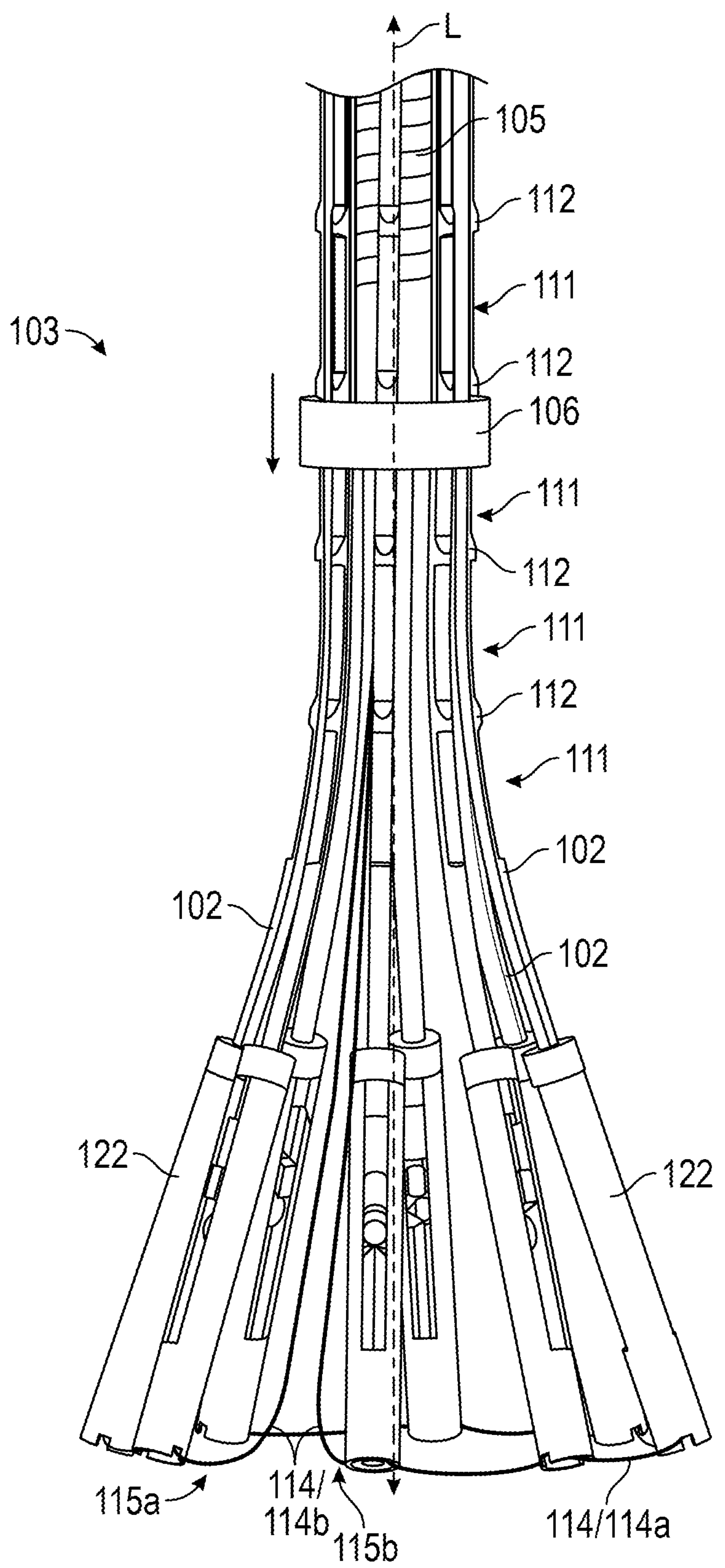

FIGS. 2A and 2B are enlarged views of the distal assembly 103 in first and second positions, respectively, in accordance with several embodiments of the present technology. As shown, the distal assembly 103 can comprise a coupler 106, plurality of arms 102 extending through the coupler 106, and a plurality of anchor assemblies 122 carried by the distal end portions of the arms 102. Each of the anchor assemblies 122 houses a corresponding anchor 130 in a low-profile configuration. The distal assembly 103 further comprises a suture 114 extending between the anchor assemblies 122. Only a few of each of the foregoing components are labeled in the drawings for ease of viewing the underlying structure.

The distal assembly 103 is configured to be disposed in a low-profile configuration within the elongate shaft 120 for intravascular delivery to the treatment site (e.g., proximate a native valve annulus). In this low-profile configuration, the arms 102 can be substantially linear and extend substantially parallel to one another. Upon release from the elongated shaft 120, the arms 102 can be biased to assume a curved configuration such that each of the arms 102 extends radially away from a longitudinal axis L of the device 100. In this deployed configuration, the anchor assemblies 122 circumscribe a shape that can be modified by adjusting the positions of the arms 102. As discussed herein, each of the arms 102 is configured to be rotated and/or translated independently of the other arms 102. Additionally or alternatively, axial advancement of the coupler 106 over the arms 102 can decrease the angle between each of the arms 102 and the longitudinal axis L, thereby pulling the anchor assemblies 122 closer together. In FIG. 2A, the distal assembly 103 is shown in a first deployed configuration in which the arms 102 extend away from the longitudinal axis L of the device 100 at a first angle and the anchor assemblies 122 circumscribe a first area. In FIG. 2B, the device 100 is shown in a second deployed configuration in which the coupler 106 has been distally advanced relative to its position in FIG. 2A. The arms 102 extend away from the longitudinal axis L at a second angle, smaller than the first angle, and the distal portions 102*b* of the arms 102 circumscribe a second area smaller than the first area.

The suture 114 can be coupled to the anchor assemblies 122 and/or anchors 130 prior to delivery of the device 100 to the treatment site. For example, the suture 114 can have a looped portion 114*a* extending between the anchors 130 and/or anchor assemblies 122 about the longitudinal axis L of the device 100, and first and second tails 114*a*, 114*b* extending proximally from the ends 115*a*, 115*b* of the looped portion 114*a* back to the handle 101 (or another extracorporeal location). The proximal ends of the suture 114 can exit the handle 101 at coupler 129. In some embodiments, the handle 101 optionally includes a securing member 127 that temporarily fixes the length of the suture 114 within the device 100. The securing member 127 can be a tab, a hook, a pin, a clamp and/or any suitable means for securing the ends of the suture 114.

The arms 102 are configured to facilitate placement of the anchor assemblies 122 and/or anchors 130 in the annular tissue to reshape and/or resize the annulus. Each of the arms 102 comprises a proximal portion 102*a* and a distal portion 102*b*. The proximal portions 102*a* of the arms 102 can be coupled to a corresponding elongate member 110 (shown in FIG. 2A only) that extends proximally to the handle 101, and the distal portions 102*b* of the arms 102 can be coupled to a corresponding anchor assembly 122. Translation and/or rotation of a given elongate member 110 causes translation and/or rotation of the corresponding arm 102. The handle 101 can include a plurality of actuators (e.g., buttons, sliders, knobs, etc.), each coupled to a proximal end portion of one of the elongate members 110. Movement of a given actuator causes movement of the corresponding elongate member 110 (and thus movement of the corresponding arm 102). In some embodiments, for example as shown in FIG. 1, the actuators comprise knobs 122 coupled to the proximal end portions of the elongate members 110. The knobs 122 can have a linear extension within the handle 101 that couples to a corresponding elongate member 110. Rotation of a given knob 122 causes translation and rotation of the corresponding elongate member 110 (and thus movement of the corresponding arm 102). In some embodiments, the actuator for controlling translation and/or rotation of the elongate member 110 and/or arm 102 is a slider, and translation of the slider causes translation of the corresponding elongate member 110 and/or arm 102. According to certain embodiments, a single one of the actuators may control translation and/or rotation of two or more arms simultaneously.

Figure 25A:
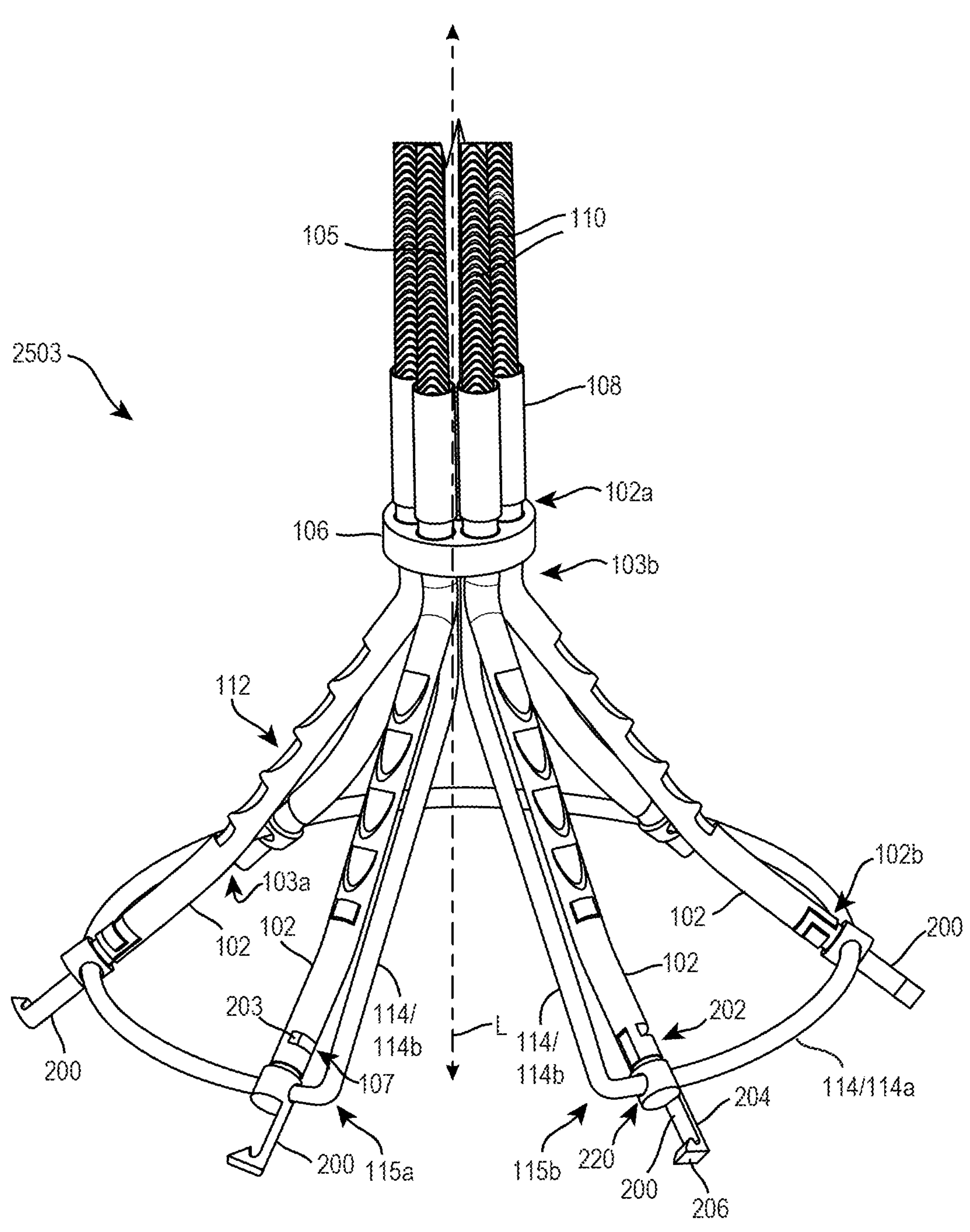
FIGS. 25A and 25B show a distal assembly configured for use with the treatment devices of the present technology, shown in first and second positions, respectively.

The individual elongate members 110 can comprise, for example, a wire, a tube (as shown in FIG. 2A), twisted wires (as shown in FIG. 25A), braided wires, a braided tube, a coil, and/or other suitable configurations. The elongate members 110 can comprise a metal or polymer material. In some embodiments, a proximal end portion 102*a* of each of the arms 102 is substantially fixed to a distal end portion of one of the elongate members 110 via a band 108 extending around both the elongate member 110 and the arm 102. The band 108 may be crimped down over the ends of the elongate member 110 and arm 102. The elongate members 110 can be coupled to the arms 102 via other securing means. For example, in those embodiments in which the elongate members 110 comprise braided or twisted wires, the elongate members 110 can be braided or twisted over the ends of the arms 102 (or, if the arms 102 are tubes, into the lumens of the arms 102) and secured with adhesive and/or a crimped band. In certain embodiments, the device 100 does not include any elongate members 110 and instead the arms 102 have a length sufficient to extend back proximally to the handle.

The distal assembly 103 shown in FIGS. 2A and 2B includes eight arms evenly spaced around the longitudinal axis L of the device 100. In some embodiments, the distal assembly 103 may include more or fewer than eight arms (e.g., two arms, three arms, four arms, five arms, six arms, seven arms, nine arms, ten arms, etc.) and/or the arms 102 may be unevenly distributed.

Figures 3A, 3B, 4A, 4B:
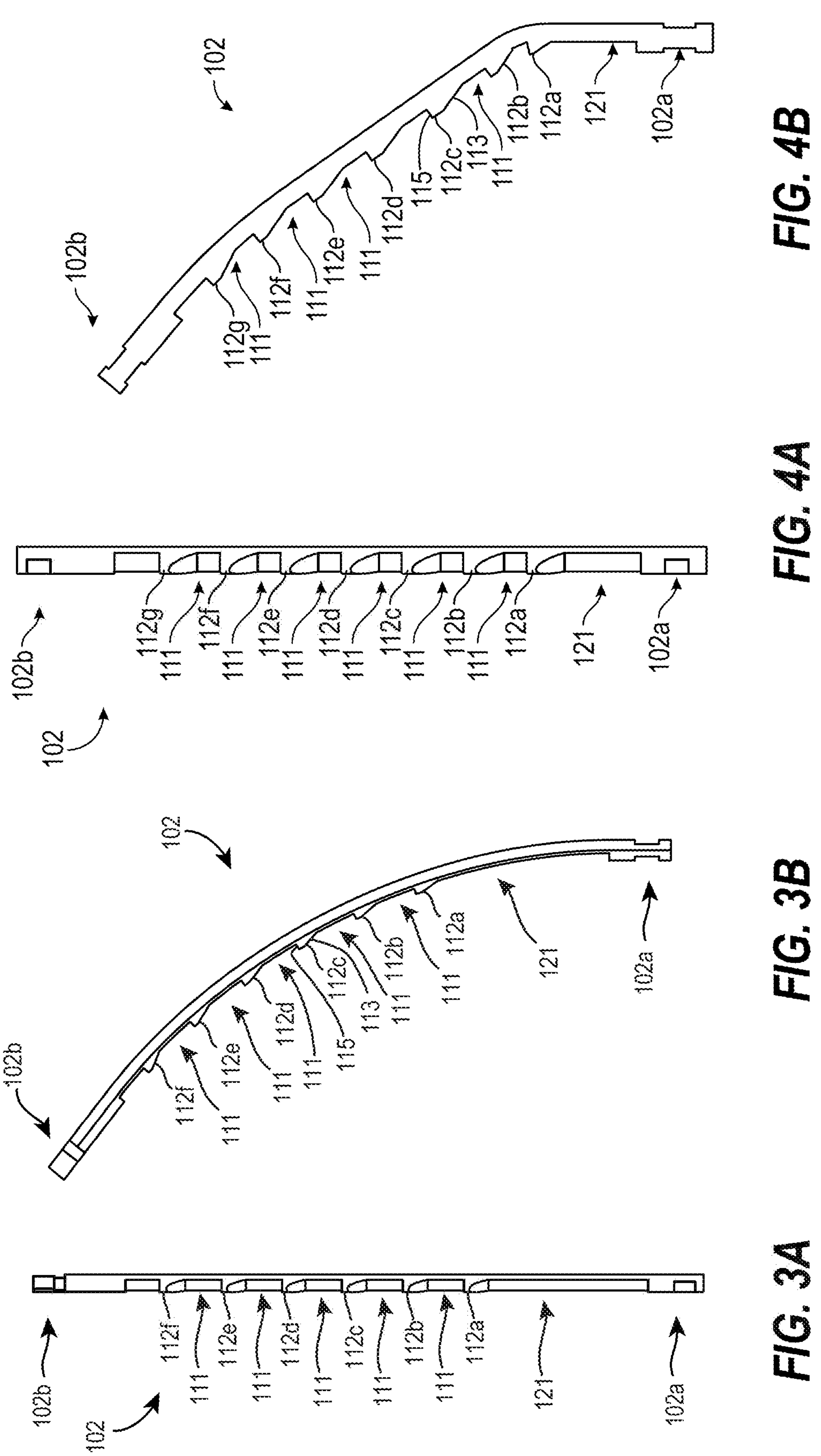
FIGS. 3A and 3B are isolated views of an arm of the distal assembly shown in FIGS. 2A and 2B, configured in accordance with several embodiments of the present technology.
FIGS. 4A and 4B are isolated views of another arm configured for use with the distal assembly shown in FIGS. 2A and 2B and configured in accordance with several embodiments of the present technology.

One, some, or all of the arms 102 can comprise an elongated element, such as a flexible tube (e.g., a metal tube, a polymer tube, a laser-cut tube, etc.), a solid rod, a ribbon, or other suitable structure. FIGS. 3A and 3B illustrate an arm 102 isolated from the distal assembly 103 shown in FIGS. 2A and 2B. The arm 102 is shown in a low-profile delivery state in FIG. 3A and a relaxed, unconstrained state in FIG. 3B. As shown, at least in the relaxed, unconstrained state, each of the arms 102 can have a preset curve and/or bend along a longitudinal axis of the respective arm 102. For example, in some embodiments some or all of the arms 102 can comprise a superelastic and/or resilient material (such as nitinol or similar metal alloys) that has been heat treated such that each of the arms 102 is configured to assume a preset curved and/or bent configuration when released from a delivery sheath (such as elongated shaft 120). The arms 102 can have a continuous radius of curvature along their lengths, or may have a varying radius of curvature. In some embodiments, a radius of curvature of the arm 102 decreases towards the distal end portion 102*b* of the arm 102.

Some or all of the arms 102 can have the same curvature, or some or all of the arms 102 can have different curvature. Likewise, some or all of the arms 102 can have the same radius of curvature, or some or all of the arms 102 can have different radii of curvature. Some or all of the arms 102 can have the same length, and some or all of the arms 102 can have different lengths. Some or all of the arms 102 can have the same cross-sectional shape, and some or all of the arms 102 can have different cross-sectional shapes. Some or all of the arms 102 can have the same cross-sectional dimension, and some or all of the arms 102 can have different cross-sectional dimensions. The curvature, length, cross-sectional shape, and cross-sectional dimension of each of the arms 102 can be selected based on the shape and/or size of the annulus to be treated.

At least some of the arms 102 comprise a first, relatively smooth side and a second side having a plurality of coupler engaging elements configured to engage arm engaging elements 117 on the coupler 106 (FIG. 5A) to secure an axial position of one, some, or all of the arms relative to the coupler 106 and/or relative to one another. In some embodiments, the corresponding engaging members of the arms 102 and coupler 106 are configured to allow movement in a single direction, similar to a ratchet. In these and other embodiments, the engaging members of the arms 102 and coupler 106 have an integrated release mechanism that enables bi-directional movement should the operator want to adjust one of the arms, as discussed in greater detail below.

In some embodiments, for example as shown in FIGS. 3A and 3B, the coupler engaging elements comprise a plurality of protrusions 112 (individually labeled 112*a*-112*f* in a proximal to distal direction) spaced apart by notches 111 along the length of the arm 102. For example, in some embodiments the arm 102 is made of a solid rod with selected portions (notches 111) removed along only one circumferential side of the rod, thereby leaving behind the protrusions 112. Because the protrusions 112 are formed of the left-behind material of the solid rod, a diameter of the arm 102 at the protrusions 112 is the same as any other portion of the rod where material has not been removed. Some or all of the arms 102 can have the same number of coupler engaging elements 112, and some or all of the arms 102 can have a different number of coupler engaging elements 112. In some embodiments, the engaging element(s) may comprise securing structures other than coupler engaging elements.

In some embodiments, for example as shown in FIGS. 3A and 3B, the most proximal notch 121 can be longer than the more distal notches 111. This provides the physician with greater freedom (relative to a notch having a shorter length) in translating the arm 102 proximally or distally before engaging the coupler 106 with the first (proximal-most) protrusion 112*a*. Likewise, the length of the proximal notch 121 dictates how far the elongate structure 105 and coupler 106 can travel from a proximalmost starting position without also moving the arms 102, as discussed below.

The protrusions 112 can have a ramped proximal surface 113 and a distal facing ledge 115. The ramped proximal surface 113 allows distal advancement of the coupler 106 over the arm 102 (or proximal movement of the arm 102 through the coupler 106), while the ledge 115 prevents proximal movement of the coupler 106 beyond the ledge 115, at least when the arm 102 is in a certain rotational orientation. The arm 102 is configured to be positioned through one of the first openings 116 in the coupler 106 (see FIG. 5A) such that the first side of the arm 102 is radially closer to the center of the coupler 106 and the second side of the arm 102 is radially closer to the edge of the coupler 106. In such an orientation, the second side of the arm 102—the side having protrusions 112—is circumferentially aligned with the arm engaging elements 117 on the coupler 106.

In some embodiments, for example as shown in FIGS. 4A and 4B, one, some, or all of the arms 102 have a preset bend 103*a* that effectively divides the respective arm 102 into a substantially linear proximal region positioned at a first angle relative to the longitudinal axis L of the device 100 and a substantially linear distal region positioned at a second angle relative to the longitudinal axis L device 100 (and angled relative to the proximal region). The second region can be distal to the first region along the longitudinal axis of the respective arm 102, and the second angle can be greater than the first angle. The distal portion can advantageously be linear to allow the anchor 130 to go inside the tube of the arm to be connected. Having a greater curvature at the bend 103*a* allows the arms 102 to extend a greater distance from the coupler 106 if necessary. In some embodiments, both the proximal and distal regions are curved, both the proximal and distal regions are linear, or the proximal region is linear and the distal region is curved. In several embodiments, the arms 102 are preset to assume a continuous or nearly continuous curve.

In some embodiments, for example as shown in FIGS. 4A and 4B, one, some, or all of the arms 102 have multiple preset bends along their respective longitudinal axes. For example, in some embodiments one, some, or all of the arms 102 can have a first preset bend 103*b* at or near the connection to the elongate member 110, and a second preset bend 103*a* along an intermediate portion of the arm 102. The first preset bend 103*b*, for example, can be disposed at a location along the longitudinal axis of the respective arm 102 that is between the proximal-most locking element and the joint between the arm 102 and the respective elongate member 110. In any of the embodiments having one or more preset bends along one or more of the arms 102, the portions of the arm 102 on either side of the bend can be substantially linear or curved.

Figure 5A:
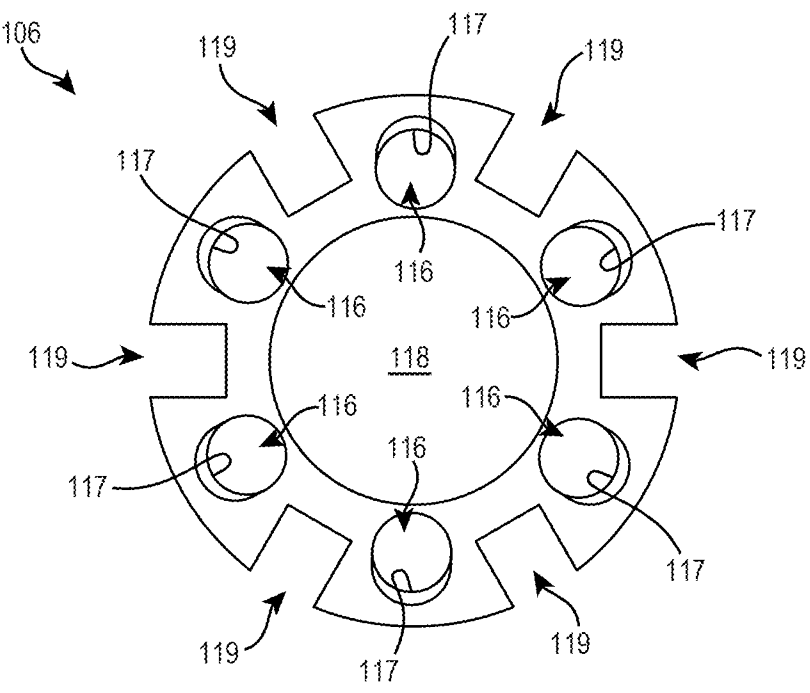
FIGS. 5A and 5B are top and perspective views, respectively, of a coupler configured for use with the treatment devices of the present technology.
Figure 5B:
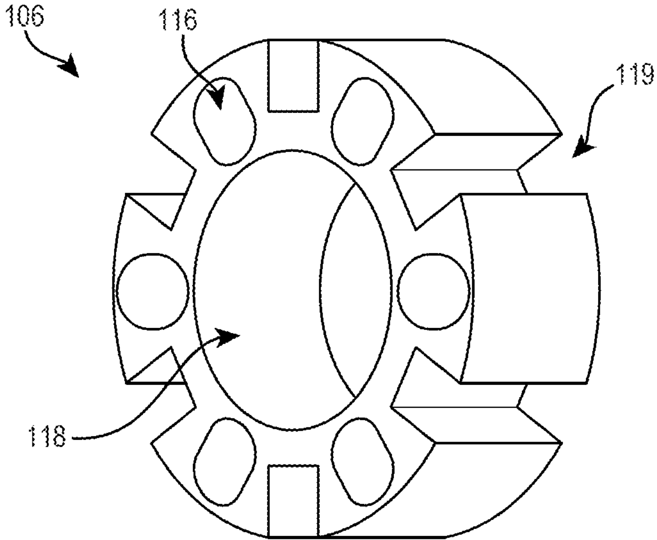

FIGS. 5A and 5B are isolated top and perspective views, respectively, of the coupler 106. The coupler 106 may be configured to hold the arms 102 in a desired spatial arrangement and inhibit axial movement of the arms 102 relative to one another once the coupler 106 has engaged one or more coupler engaging elements on the arms 102 (as detailed herein). As best shown in FIG. 2B, the device 100 can include an elongate structure 105 configured to extend between the coupler 106 and the handle 101 and provide the operator with translational and/or rotational control of the coupler 106. For example, the elongate structure 105 can have a proximal end portion coupled to a slider 126 (or any other actuator) on the handle 101 (FIG. 1) and a distal end portion fixed to the coupler 106. The elongate structure 105 can extend through the elongate shaft 120 generally parallel to the elongate members 110. Translation of the slider 126 causes translation of the elongate structure 105, thereby causing translation of the coupler 106. In some embodiments, the actuator for controlling translation of the elongated structure 105 and/or coupler 106 is a knob, and rotation of the knob causes translation of the elongated structure 105. From a starting, proximalmost position, distal translation of the elongate structure 105 and coupler 106 does not also move the arms 102 distally. When the coupler 106 reaches the first notch on the arms 102, however, continued distal movement of the coupler 106 pushes the arms 102 forward, thereby expelling the arms 102 (and distal assembly 103) from the elongate shaft 120. To move the coupler 106 distally over the arms 102 (to engage coupler engaging elements 112), one or more actuators 124 on the handle 101 can be actuated to releasably fix the axial and/or rotational positions of the arms 102 relative to the handle 101. The handle 101 can include an actuator 124 for each of the arms 102 so that the axial position of each arm 102 relative to the coupler 106 can be independent of the axial positions of the other arms 102. In some embodiments, a single actuator 124 can axially and/or rotationally fix two or more arms 102 simultaneously. The actuators 124 can be a screw, a knob, a clamp, a button, and/or other releasable fixation means.

Figures 6A, 6B:
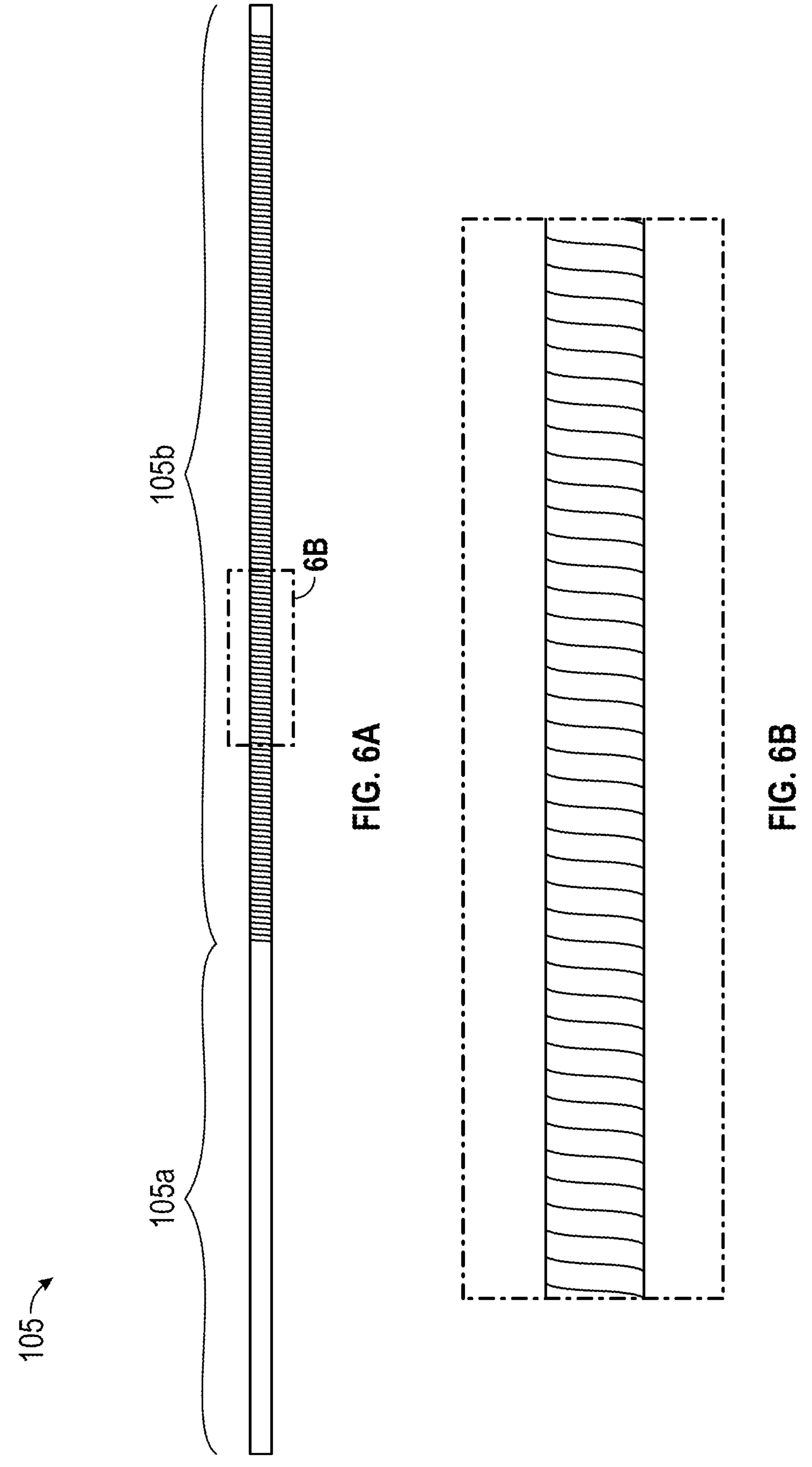
FIG. 6A is a side view of a manipulation member configured in accordance with several embodiments of the present technology.
FIG. 6B is an isolated view of a distal portion of the manipulation member shown in FIG. 6A.

The elongate structure 105 can be a solid rod or a hollow tube. In those embodiments where the elongate structure 105 is a hollow tube, the suture 114 (and/or other components) can extend from the handle 101 to the distal assembly 103 through the lumen of the elongate structure 105. In some embodiments, for example as shown in FIGS. 6A and 6B, the elongate structure 105 comprises a laser cut tube. The distal end portion of the tube can be fixed to the coupler 106 (e.g., via welding, adhesive, snap fit, friction fit, crimp, or other suitable attachment means) and the proximal end portion can be coupled to the handle 101. The tube can have a first, more proximal portion 105*a* that does not include any cuts, and a second, more distal portion 105*b* that comprises a series of circumferentially-extending cuts that increases the flexibility of the tube along that portion. This increased flexibility enables the elongate structure to track around the sharp turns near and in the heart. In some embodiments, the angle of the laser cut is between about 0.1 degrees and about 20 degrees. The uncut portions are also designed to be alternating about 90 degrees from each other which allows the tube to bend in multiple directions.

In some embodiments, the elongate structure 105 comprises an elongate shaft having a lumen configured to slidably receive the elongate members 110 such that the elongate shaft surrounds the elongate members 110. In such embodiments, the elongate shaft can have a diameter substantially equivalent to a diameter of the coupler 106 such that a distal end of the elongate shaft is coupled to the coupler 106 around a circumference of the coupler 106.

As shown in FIGS. 5A and 5B, the coupler 106 can comprise a disc having a plurality of openings extending therethrough. The plurality of openings can include one or more first openings 116 and one or more second openings 118. Each of the first openings 116 can be configured to receive one of the arms 102 partially or completely therethrough. The second opening 118 can be configured to receive a distal end portion of the elongate structure 105, as detailed herein. Additionally or alternatively, the second opening 118 can be configured to receive one or more other components of the system therethrough, such as an imaging element for better visualization during the procedure, a locking catheter configured to lock the suture in position before the device is removed, a suture 114, a cutting catheter, a locking and cutting catheter, etc. In some embodiments, the coupler 106 can include additional openings. In FIGS. 5A and 5B, the first openings 116 are evenly spaced about the circumference of the coupler 106 and the single second opening 118 is positioned at a more central portion of the coupler 106. In some embodiments, the first and second openings 116, 118 can have other arrangements, for example as described herein with reference to FIGS. 14-24C.

It will be appreciated that the elongate structure 105 can engage and/or be coupled to the coupler 106 at other, non-central locations. For example, in some embodiments the coupler 106 includes a third opening (not shown) configured to receive and/or be coupled to a distal portion of the elongate structure 105, and the second opening 118 (whether located centrally or otherwise) can be configured to receive a suture locking device therethrough. In some embodiments, the elongate structure 105 can comprise one or more coupler engaging elements configured to engage the coupler 106 and secure an axial position of the elongate structure 105 relative to the coupler 106. The coupler engaging elements can be similar to any of the coupler engaging elements described herein with reference to the arms 102.

Figure 14:
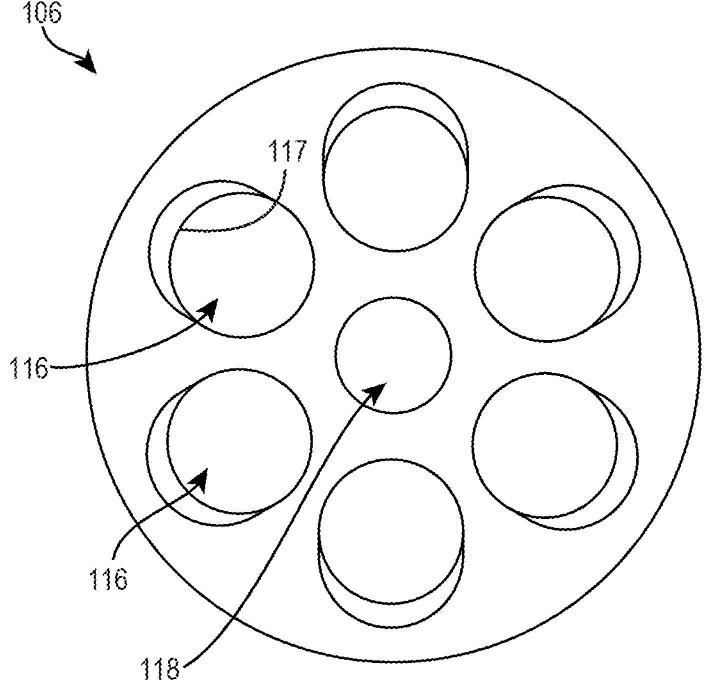
FIGS. 14-22, 23A-23C, and 24A-24C show different coupler configurations in accordance with several embodiments of the present technology.

In some embodiments, the coupler 106 can comprise one or more recesses 119 extending radially inwardly from an outer edge of the coupler 106. The recesses 119 can be configured to receive wires, shafts, or other components passing through from the handle 101 to the distal portion 100*b* of the device 100. The recesses 119 can be positioned between adjacent first openings 116 such that the coupler 106 comprises alternating recesses 119 and first openings 116 in a circumferential direction. In some embodiments the coupler 106 does not include any recesses 119, for example as shown in FIG. 2A and FIG. 14.

As best shown in FIG. 5A, the coupler 106 can include one or more engaging elements configured to engage one or more coupler engaging elements of the arms 102 and/or the elongate structure 105. For example, the coupler 106 can include one or more arm engaging elements 117 disposed within one, some, or all of the first openings 116. The arm engaging elements 117 can be configured to engage with one or more coupler engaging elements 112 and/or other portions of the arms 102, thereby creating a reversible ratcheting means for axial movement of the coupler 106 relative to the arms 102. Each arm engaging element 117 is configured to allow rotation and translation of the arms 102 as desired while also enabling selective engagement of the arms 102 to inhibit proximal movement of the arms 102. As previously discussed, one, some, or all of the coupler engaging elements 112 of a particular arm 102 can be disposed at only one side of the arm 102, and the arm engaging element 117 of the coupler 106 can comprise a ridge that is disposed along only a portion of the inner surface defining the corresponding first opening 116. As such, the coupler engaging elements 112 of the arms 102 only engage the arm engaging elements 130 in the first openings 116 (and lock in place) when the coupler engaging element 112 of the arm 102 is circumferentially aligned with the arm engaging element 117 in the first opening 116. One, some, or all of the arms 102 can be shape set to include one or more bends (for example, as described herein) that encourage and/or further secure engagement with the arm engaging elements 117. For example, one, some, or all of the arms 102 may be biased radially outwardly so that the arms 102 are urged towards the arm engaging elements 117 (or any other engaging element) when the arm 102 is positioned in the correct orientation. If the arm 102 is rotated such that the coupler engaging element 112 is out of alignment with the arm engaging element 117, the arm 102 becomes decoupled from the arm engaging element 117 and can move axially relative to the first opening 116. The ability to decouple the arms 102 from the coupler 106 enables repositioning of one or more arms 102 of the device 100, which can be beneficial, for example, when the operator wants to pull back and reposition an arm 102 as needed.

Once the arms 102 are positioned at desired locations relative to the annular tissue (such as the supra-annular tissue) and the anchor assemblies 122 are proximate and/or in contact with the tissue, the axial and/or rotational positions of the arms 102 can be fixed (e.g., via actuators 124) and the coupler 106 can be advanced distally over the arms 102, thereby pulling the arms 102 toward one another and (at least temporarily) locking the arms 102 in place as the arm engaging elements 117 of the coupler 106 engage the coupler engaging elements 112 of the arms 102.

The arm engaging elements 117 can have any number of shapes and may be positioned at any circumferential and/or axial position within the first openings 116. For example, as shown in FIG. 5A, one, some, or all of the arm engaging elements 117 can have a radially-inner surface that extends along a substantially curved path. In some embodiments, the arm engaging elements 117 can have a radially-inner surface that extends along a substantially linear path. In some embodiments, one, some, or all of the arm engaging elements 117 have a radially-inner surface having one or more portions extending along a substantially curved path and one or more portions extending along a generally linear path. In some embodiments, the arm engaging elements 117 comprise a single protrusion within a corresponding first opening 116. In some embodiments, the arm engaging elements 117 comprise multiple protrusions within a particular first opening 116. One, some, or all of the first openings 116 can have the same number of arm engaging elements 117. One, some, or all of the first openings 116 can have a different number of arm engaging elements 117. The arm engaging elements 117 in one, some, or all of the first openings 116 can have the same shape. The arm engaging elements 117 in one, some, or all of the first openings 116 can have different shapes. The arm engaging elements 117 in one, some, or all of the first openings can be positioned at and/or span generally the same circumferential location and/or have the same arc length. The arm engaging elements 117 in one, some, or all of the first openings 116 can be positioned at and/or span different circumferential locations and/or have different arc lengths. The arm engaging elements 117 may extend along no more than 180 degrees of the first opening 116, or no more than 160 degrees, no more than 140 degrees, no more than 120 degrees, no more than 100 degrees, no more than 90 degrees, no more than 80 degrees, no more than 60 degrees, no more than 45 degrees, no more than 30 degrees, no more than 20 degrees, no more than 10 degrees, no more than 5 degrees, no more than 4 degrees, no more than 3 degrees, no more than 2 degrees, or no more than 1 degree. In some embodiments, one, some, or all of the arm engaging elements 117 may span 360 degrees or more. In some embodiments, one, some, or all of the first openings 116 do not include arm engaging elements 117.

According to some aspects of the technology, the coupler 106 additionally or alternatively includes one or more elongate structure engaging elements within the second opening (s) 118. For example, in some embodiments the coupler 106 has one or more ridges within one or more of the second openings 118 and/or other openings in the coupler 106. The elongate structure engaging elements can interface with coupler engaging elements on the elongate structure 105 in a manner similar to that described above with respect to the arm engaging elements and coupler engaging elements on the arms.

The coupler 106 is configured to hold a portion of the arms 102 radially together, with each of the arms 102 having a length proximal to the coupler 106 and a length distal to (and cantilevered from) the coupler 106. In some embodiments, the arms 102 are configured to slide axially through the openings, for example in response to axial movement of a corresponding elongate member 110. Additionally or alternatively, the arms 102 can rotate within their respective openings, for example in response to rotation of the corresponding elongate member 110.

One, some, or all of the arms 102 can be configured to move independently of one another, thereby enabling independent adjustment of each anchor assembly 122 and/or anchor 130 of the device 100. This provides the operator with localized geometric control to customize the size and the site of anchoring. In some embodiments, one, some, or all of the arms 102 are configured to rotate about their own longitudinal axis independent of one another. Additionally or alternatively, one, some, or all of the arms 102 may be configured to move axially relative to one another.

In some embodiments, the elongate shaft 120 is steerable. The device 100 can comprise an elongate member (not visible) extending between a distal end portion of the elongate shaft 120 and an actuator 128 at the handle 101. The elongate member can be a wire, a suture, a tubular member, etc. Rotation of the actuator 128 in a first direction pulls on the elongate member, thereby causing deflection and/or bending of the elongate shaft 120. Rotation of the actuator 128 in a second direction releases tension on the elongate member, thereby straightening the elongate shaft 120. In some embodiments, the actuator 128 actuates the elongate member via translation (and not rotation). In some embodiments, the actuator 128 actuates the elongate member via translation and rotation. In some embodiments, the device 100 comprises a second elongate member extending between a distal end portion of the elongate shaft 120 and a second actuator (not shown) at the handle 101. Tension on the second elongate member can cause deflection and/or bending of the elongate shaft 120 in a different direction than the direction of deflection and/or bending caused by the elongate member coupled to actuator 128.

As previously mentioned, each of the anchors 130 and/or anchor assemblies 122 can be carried by a different one of the arms 102. In some embodiments, each of the anchors 130 may be detachably coupled to a corresponding one of the arms 102 such that, upon completion of treatment, the arms 102 may be removed from the patient (along with the rest of the device 100) while only the anchors 130 and suture 114 remain implanted at the annulus. For example, the anchors 130 can be mechanically or electrolytically detachable from the distal portions 102*b* of the arms 102. In some embodiments, the handle 101 includes an actuator that, when triggered by the operator, causes one, some, or all of the anchors 130 to release from a corresponding arm 102.

Figure 7:
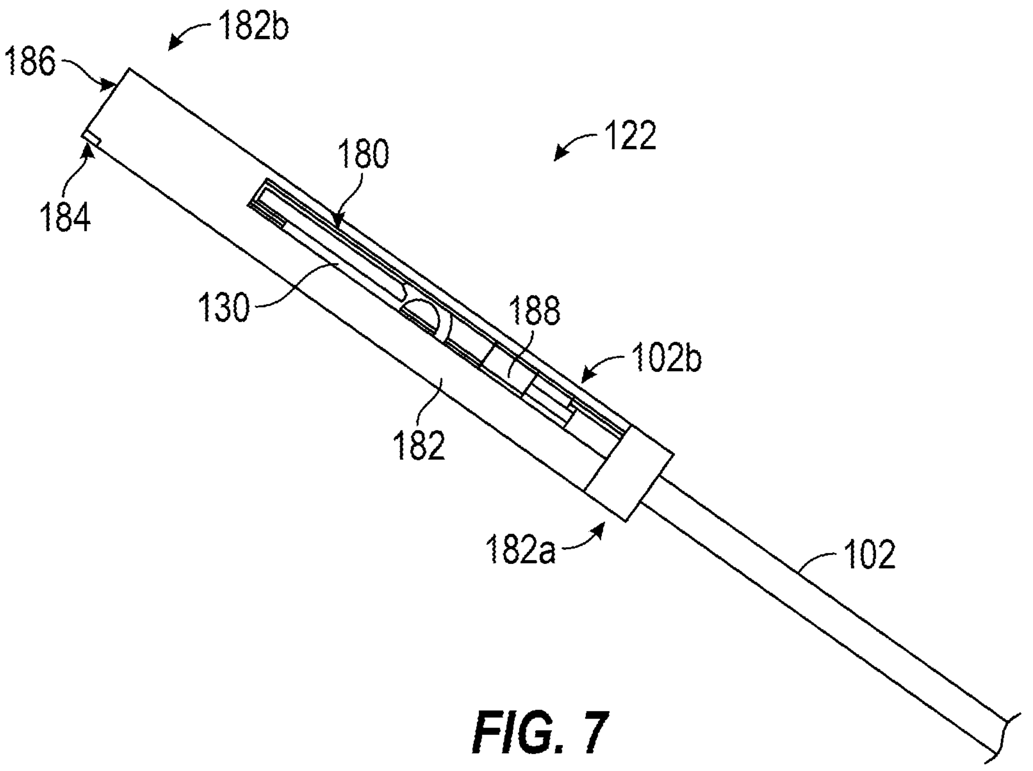
FIGS. 7 and 8 are perspective and cross-sectional views, respectively, of an anchor assembly configured for use with the treatment devices of the present technology.
Figure 8:
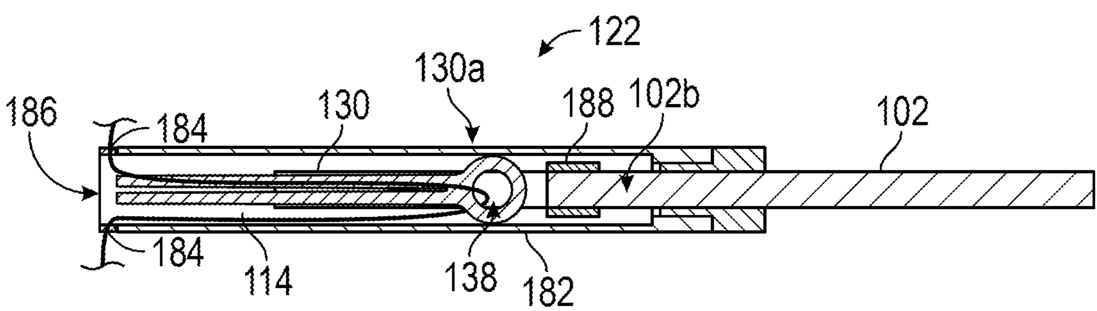

FIGS. 7 and 8 are perspective and cross-sectional views of an anchor assembly 122. The anchor assembly 122 can comprise a cylindrical housing 182 coupled to the distal end portion 102*b* of a corresponding arm 102 and an anchor 130 disposed partially or completely within the housing 182. In general, the anchor assembly 122 is configured to carry the anchor 130 to the treatment site and facilitate insertion of the anchor 130 into the tissue at a desired location. In some embodiments, the anchor assembly 122 is configured to contain the anchor 130 within a lumen of the housing 182 until the arm 102 exerts enough axial force on the anchor 130 to expel the anchor 130 from the housing 182.

As shown in FIGS. 7 and 8, the housing 182 has a proximal end portion 182*a* and a distal end portion 182*b*. The proximal end portion 182*a* of the housing 182 defines an opening through which the distal end portion 102*b* of the arm 102 extends. The distal end portion 182*b* defines an opening 186 through which the anchor 130 is configured to pass, in a low-profile state, when the anchor 130 is expelled from the housing 102. In some embodiments, the housing 182 optionally includes diametrically opposed notches 184 extending proximally from the distal end surface. The notches 184 can be configured to receive incoming and outgoing lengths of the suture 114 (shown only in FIG. 8) to help guide the path of the suture 114 between adjacent anchor assemblies 122. The housing 182 can comprise a cylindrical sidewall defining a lumen that is configured to receive the anchor 130 in a substantially linear, low-profile delivery state. The lumen may be sized such that the anchor 130 remains within the lumen based on friction forces between the anchor 130 and an inner surface of the housing 182. In some embodiments, the anchor 130 is biased to assume a curved configuration when released from the housing 182 and thus continually presses outwardly against the inner surface of the housing 182 when contained therein. The housing 182 can include a slot 180 extending along at least a portion of its length that is configured to receive a guide 188 that is coupled to a distal end of the arm 102. The guide 188 can be configured to slide along and within the slot 180, thereby preventing rotation of the arm 102 relative to the housing 182. In some embodiments, the arm 102 is configured to rotate relative to the housing 182 (or vice versa). For example, in some embodiments the housing 182 does not include the slot 180 and/or the arm 102 does not include the guide 188.

In use, the operator pushes the distal end surface of the housing 182 into contact with the annular tissue at a desired anchor insertion site (e.g., by distal advancement of the corresponding arm 102). While the tissue resists distal movement of the housing 182, the operator continues to push the corresponding arm 102 distally, thereby forcing distal movement of the arm 102 relative to the housing 182. As the arm 102 moves distally within the housing 182, the arm 102 pushes the anchor 130 through the distal opening of the housing 182 and into the tissue.

In some embodiments, the device 100 includes an elongated member (e.g., a wire, a tube, etc.) (not shown) having a distal end portion coupled to the anchor 130 and a proximal end portion coupled to the handle 101. For example, a distal portion of the elongated member can extend through the opening 138 in the anchor 130 and/or otherwise be coupled to a proximal portion 130*a* of the anchor 130, then extend proximally back to the handle 101 through a lumen of the arm 102 (if the arm 102 includes a lumen) or along the arm 102. If the operator is not happy with the deployment of the anchor 130, the physician can pull back on the elongated member to pull the anchor 130 proximally out of the tissue and back into the housing 182. For any of the anchors discussed with reference to FIGS. 9 and 31A-35, withdrawal of the anchor 130 into the housing 182 straightens the bend of the anchor 130 and forces the anchor 130 into a radially collapsed and/or substantially linear profile that fits within the lumen of the housing 182.

Upon completion of treatment, the arms 102 may be removed from the patient (along with the rest of the device 100) while only the anchors 130 and suture 114 remain implanted at the annulus. Detachability of the anchors 130 is particularly advantageous as it enables treatment with less hardware remaining in the patient as compared to conventional devices, such as the IRIS Transcatheter Annuloplasty Ring System (Boston Scientific, Marlborough, Massachusetts). The detachability of the anchors 130 also allows the physician to perform valve replacement procedures or edge-to-edge repair in the future. Typical edge-to-edge repair therapies for FMR (such as MitraClip™, Abbott Cardiovascular, MN, USA) do not allow room for future interventions to fix the valve). In some embodiments, one or more of the anchors 130 can be fixed (i.e., non-detachable) to the corresponding arm 102.

Figure 9:
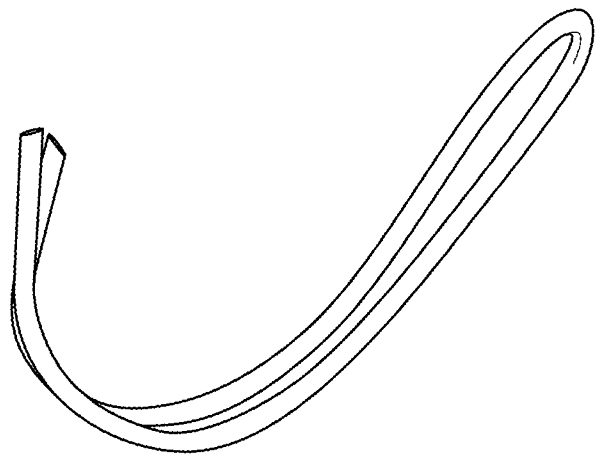
FIG. 9 is an enlarged, isolated view of an anchor configured in accordance with the present technology.

FIG. 9 is an isolated view of an anchor 130 configured in accordance with the present technology. The anchor 130 comprises a proximal portion 130*a* configured to be coupled to the suture 114 and a distal portion 130*b* configured to penetrate and be embedded in annular tissue. The proximal portion 130*a* comprises an opening 138 configured to receive the suture 114 therethrough. In some embodiments, the proximal portion 130*a* and/or opening 138 can be configured to be detachably coupled to a component of the device 100 (e.g., a distal end portion of the arm 102, a portion of the anchor assembly 122, a portion of the anchor assembly housing 182, etc.). As shown in FIG. 9, the anchor 130 can comprise at least two arms 132, all or a portion of which are configured to be embedded within the tissue. Each of the at least two arms 132 has a distal tip 136 configured to penetrate the annular tissue. In some embodiments, the distal tips 136 are beveled to provide a sharpened surface. In other embodiments, the distal tips 136 are blunt.

In some embodiments, including those depicted by FIG. 9, the anchor 130 can be formed of an elongate member, such as a wire, that is bent back on itself to form the opening 138. The wire can have a circular, rectangular, square-shaped, or other cross-sectional shape. The proximal ends of the arms 132 are continuous at the bend, and the distal ends correspond to the distal end portion 130*b* of the anchor 130. The elongated member can be formed of a superelastic and/or resilient material, such as nitinol, cobalt chromium, and/or alloys thereof. The wire can have a diameter of about 0.30 mm to about 0.50 mm, about 0.35 mm to about 0.45 mm, about 0.40 mm to about 0.45 mm, about 0.40 mm, about 0.43 mm, or about 0.45 mm. While using a larger diameter wire increases the overall surface area and strength of the wire, such robustness also increases the friction between the anchor 130 and the anchor assembly housing 182 and makes it more difficult to push the anchor 130 from the housing 182. For example, all else equal, the inventor found that an anchor formed using a 0.43 mm or greater wire was significantly harder to deploy than an anchor formed of a 0.40 mm wire. As discussed below with reference to FIGS. 33-35, in some embodiments the anchor 130 is cut from a sheet of material (including superelastic and/or resilient materials). In any case, the elongated member can be shape set (e.g., via a heat treatment) such that the elongated member is biased to assume a desired curved shape when released from the housing 182 of the anchor assembly 122. In some embodiments, the elongated member can be shape set such that the plane of the opening 138 is about 90 degrees from the direction along which the distal tips 136 are extending.

As shown in FIG. 9, in some embodiments the arms 132 may cross over one another between the proximal and distal portions 130*a*, 130*b* of the anchor 130 while still extending along generally the same path. The intersection 134 between the arms 132 can provide additional structural support to the tissue-engaging portion of the anchor 130, thereby improving fixation with the tissue. In some embodiments, the arms 1302 do not cross between the proximal and distal end portions 130*a*, 130*b* of the anchor 130, for example as shown with reference to FIGS. 32C and 32F.

Figure 10:
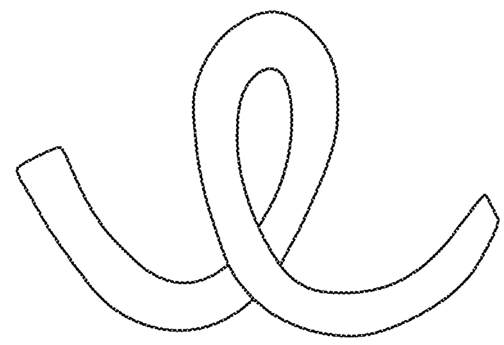
FIG. 10 is an enlarged, isolated view of a prior art anchor.

To demonstrate the superior performance of the anchors 130 of the present technology relative to existing anchors, the inventor performed a tensile pull test on ten samples of the anchor design shown in FIG. 9 (the "test anchor") and two groups of samples of the prior art anchor design shown in FIG. 10. Unlike the test anchor, the legs of the prior art anchor diverge laterally after crossing. One of the prior art groups comprised eight samples that were made using a 0.40 mm nitinol wire (the "Group I"), and the other prior art group comprised seven samples made using a 0.45 mm nitinol wire (the "Group II"). The test anchor was made from a 0.40 mm nitinol wire. The testing was conducted using an AMETEK DFE II force gauge. Anchors were inserted into a sheep heart using a single arm and anchor assembly. The ends of the anchors were pre-attached with a suture. Once the anchors were implanted in the tissue, the loose end of the suture was attached to the force gauge and was pulled to measure the force. The maximum force required to pull the anchor all the way out of the tissue was then recorded and the results are seen in Table 1 below.

As demonstrated, the anchor designs of the present technology can support 1.75× the maximum load of the prior art anchors. This was true even with the increased wire size of Group II.

TABLE 1

| Sample # | Test Anchor (lbF) | Group I (lbF) | Group II (lbF) |
|---|---|---|---|
| 1 | 1.35 | 0.65 | 0.88 |
| 2 | 1.58 | 0.83 | 0.75 |
| 3 | 1.25 | 0.63 | 0.63 |
| 4 | 1.39 | 0.65 | 0.72 |
| 5 | 1.21 | 0.79 | 0.76 |
| 6 | 1.93 | 0.78 | 0.86 |
| 7 | 1.23 | 0.84 | 0.79 |
| 8 | 1.03 | 0.88 | — |
| 9 | 1.01 | — | — |
| 10 | 1.17 | — | — |
| Total Samples | 10 | 8 | 7 |
| Avg | 1.32 | 0.76 | 0.77 |
| Std. Dev. | 0.27 | 0.1 | 0.084852814 |

In use, the device 100 can be intravascularly positioned at or proximate a native valve annulus, such as a heart valve annulus, with the arms 102 contained in a delivery sheath in a low-profile delivery configuration. In some embodiments, the arms 102 can be released from the constraints of the delivery sheath by pushing the arms 102 through the opening at the distal end of the elongated shaft 120. For example, as previously discussed, the coupler 106 can be advanced distally until it engages a proximal portion of the arms 102, at which point continued axial advancement of the coupler 106 also advances the arms 102 (so long as the arms are not fixed axially by one or more actuators, as discussed above). In some embodiments, the elongated shaft 120 can be pulled proximally to expose the arms 102, thereby allowing the arms 102 to extend radially away from the longitudinal axis L of the device 100 into a deployed configuration. In any case, the device 100 can be deployed proximate to and above the annulus such that the anchor assemblies 122 are positioned proximate the annular tissue just above the plane of the valve orifice.

The arms 102 can be independently adjusted to precisely position each anchor 130 in accordance with the particular valve geometry. As such, the devices 100 of the present technology are configured to treat a wide variety of annulus shapes and sizes. Once the anchor assemblies 122 and/or anchors 130 are in a desired position relative to the annular tissue, the arms 102 can be advanced distally to force the anchors 130 out of the anchor assemblies 122 and into the annular tissue. Each of the arms 102 can be advanced separately to deploy the anchors 130, or some or all of the arms 102 can be advanced simultaneously to simultaneously deploy the anchors 130. For example, in some embodiments, axial movement and/or rotation of the coupler 106 rotates all of the arms 102 simultaneously such that the anchors 130 engage and/or embed within the tissue at substantially the same time, thereby saving procedural time. In some embodiments, the operator may deploy an anchor 130 for a first one of the arms 102, then adjust a position of a second one of the arms 102 before deploying the anchor 130 associated with the second one of the arms 102. In some embodiments, one or more of the arms 102 can be translated and/or rotated to partially or completely remove the anchors 130 from the tissue.

When the anchors 130 have been sufficiently secured to the annular tissue, the coupler 106 can be moved relative to the arms 102 (or vice versa) to pull together the arms 102 and reshape and/or resize the annulus. In general, advancing the coupler 106 distally relative to the arms 102 decreases an angle and/or a circumferential distance between a) adjacent arms and/or b) adjacent anchors. Likewise, advancing the coupler 106 distally relative to the arms 102 decreases an angle between the individual arms 102 and the longitudinal axis L. In some embodiments, the coupler 106 can be advanced distally over the arms 102 until engaging at least a first (or most proximal) level of coupler engaging elements 112 along the arms 102. The stepped surface of the coupler engaging elements 112 prevent the coupler 106 from moving proximally beyond the grooves 112, thus limiting axial movement between the coupler 106 and the arms 102. Regardless of engagement of the coupler 106 with the coupler engaging elements 112, the arms 102 maintain the ability to rotate within their respective openings within the coupler 106. Moreover, as previously discussed, in some embodiments the arms 102 can be rotated within their respective openings to unlock their axial positions. Should the operator desire to decrease the area of the annulus even further, the coupler 106 can be advanced distally over the arms 102 until engaging at least a second level of coupler engaging elements 112 along the arms 102 distal of the first level of coupler engaging elements 112. In some embodiments, the coupler 106 and at least one of the arms 102 can be held in place while one or more of the other arms 102 are pulled proximally to engage the next level of coupler engaging elements 112. As such, depending on the needs of the particular modification, the coupler 106 is configured to engage different levels of grooves on different arms 102. For example, the coupler 106 can simultaneously engage a first coupler engaging element level 112 on one of the arms 102 and a second coupler engaging element level 112 on another one of the arms 102.

Figure 11A:
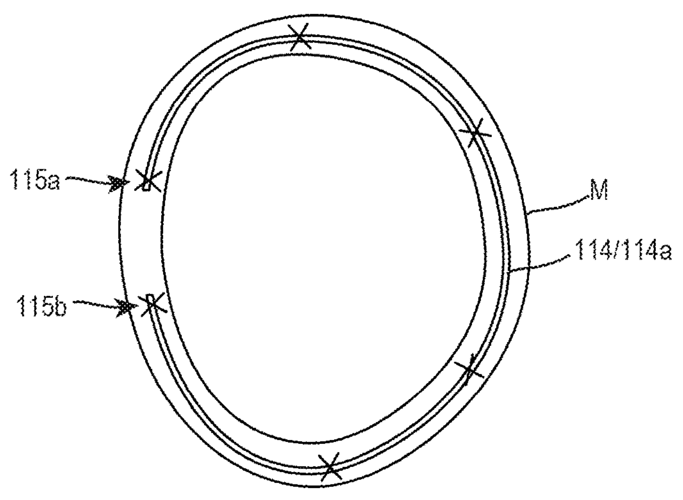
FIGS. 11A-11C are schematic depictions of a suture coupled to an annulus, shown in open and closed configurations in accordance with several embodiments of the present technology.

FIG. 11A schematically depicts the looped portion 114*a* of the suture 114 extending around the valve annulus, prior to the arms 102 and/or anchors 130 modifying the size and/or shape of the annulus. The locations of the anchors 130 are denoted by X's, and the suture tails 114*b* are not shown. Once the anchors 130 have penetrated and are secured to the tissue and the shape and/or size of the annulus has been modified (e.g., by the coupler 106 pulling the arms 102 inwardly), the perimeter of the annulus is less than prior to the modification, and thus some slack 123 will be present in the looped portion 114*a* of the suture 114. In some embodiments, the slack in the suture 114 can be removed as the arms 102 pull the annulus together, for example by the operator pulling the exposed end of the suture 114 extending from the coupler 129 on the handle 101 (FIG. 1). In either case, the suture 114 is only passively involved in modifying the annular shape and/or size since it is the arms 102 of the device that provide the inward force that modifies the shape and/or size of the annulus. As demonstrated schematically in FIGS. 13A and 13B, this is in contrast to several prior art devices that cinch the suture to pull the annular tissue together.

Figure 11B:
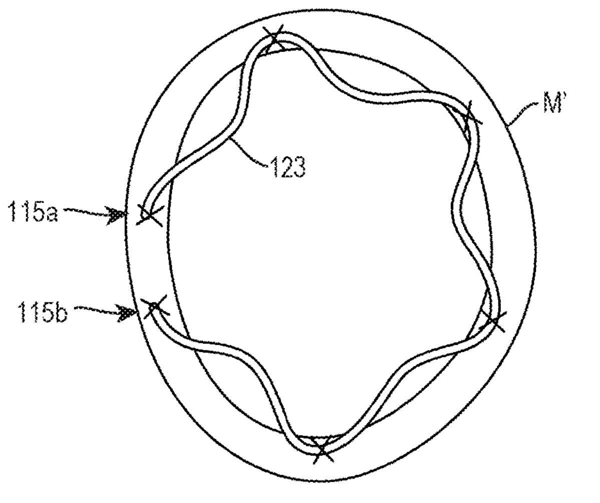
Figure 11C:
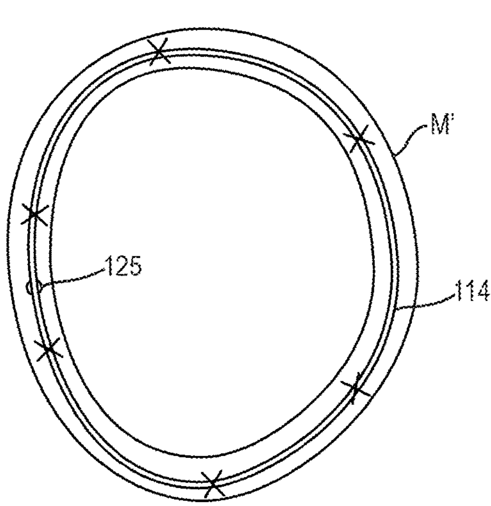
Figure 12:
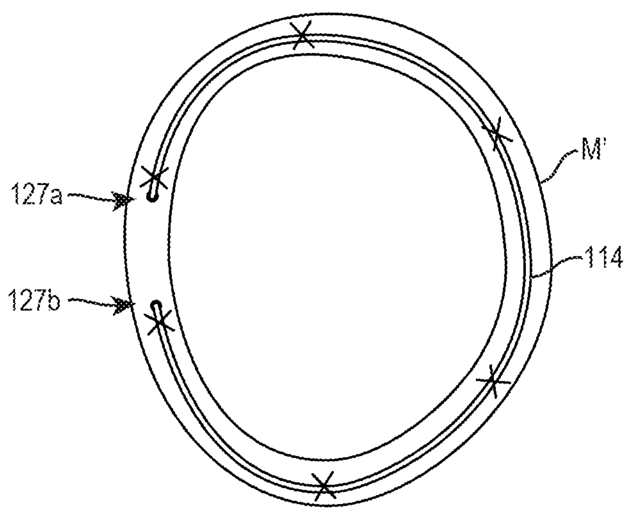
FIG. 12 schematically depicts a suture coupled to an annulus, shown in a closed configuration in accordance with several embodiments of the present technology.
Figure 13A:
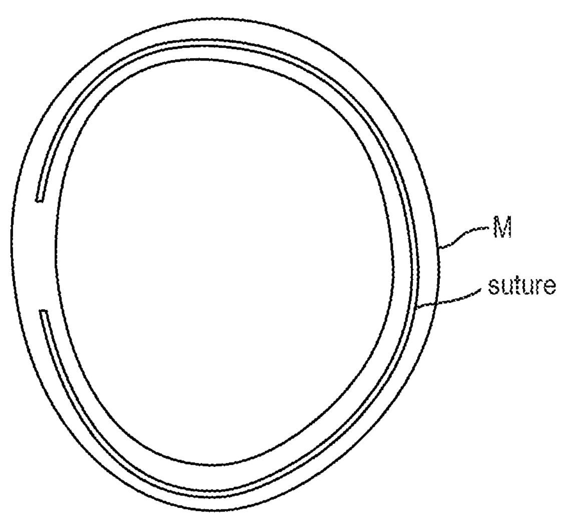
FIGS. 13A and 13B are schematic depictions of a suture of the prior art in an open and closed configuration.
Figure 13B:
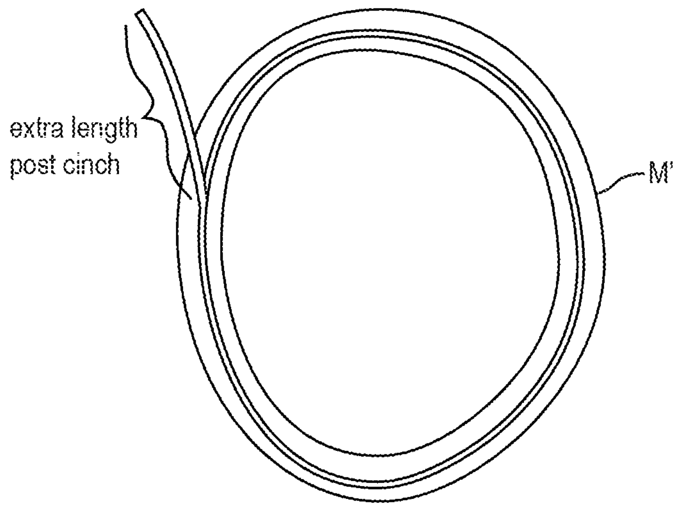

Once the valve annulus has been modified by the arms 102 and/or anchors 130 into a desired shape and/or size, a length of the suture 114 extending between the anchors 130 can be adjusted to approximate the new, shorter length of the perimeter of the annulus (as shown in FIG. 11B). The suture 114 can then be fixed at that length so that, upon removal of the arms 102 and rest of the device, the suture 114 holds the anchors 130 in the modified shape. For example, the device 100 can include an elongate shaft (not shown) configured to be advanced distally over the tails 114*b* of the suture 114, thereby bringing together the more distal portions of the tails 114*b*. One example of an elongate shaft is the finishing device disclosed herein. Other devices are possible. The elongate shaft can be advanced until a distal end portion of the elongate shaft is positioned where the tails branch into the looped portion of the suture 114. The device 100 may further include a locking means (either incorporated into the elongate shaft or separate from the elongate shaft) that effectively ties, knots, or otherwise fixes a length of the suture 114, for example as shown by locking element 125 in FIG. 11C. With reference to FIG. 12, in some embodiments, the device 100 can include locking elements 127*a*, 127*b* (shown schematically) delivered (for example, via an elongate shaft) proximate the openings 138 in the anchors 130 at the ends 115*a*, 115*b* of the looped portion 114*a*. The locking elements 127*a*, 127*b* can be secured to the suture 114 and have a cross-sectional dimension greater than a cross-sectional dimension of the openings 138 in the anchors 130. As such, once in place, the locking elements 127*a*, 127*b* prevent movement of the suture 114 through the openings 138. In some embodiments, the locking elements are incorporated into the arms 102, anchor assemblies 122, anchors 130, and/or suture 114 and can be manipulated into a locking position by a tool advanced to the treatment site. In any case, the suture 114 may then be cut with the elongate shaft (or another tool, such as one of the finishing devices disclosed herein) to remove the remaining suture 114 from the treatment site.

I. Additional Embodiments

FIG. 14 is a top view of a coupler 106 for use with the treatment devices 100 of the present technology. The coupler 106 can be substantially identical to coupler 106 described with respect to FIGS. 5A and 5B, except coupler 106 does not include recesses cut into its circumferential edge.

Figure 15:
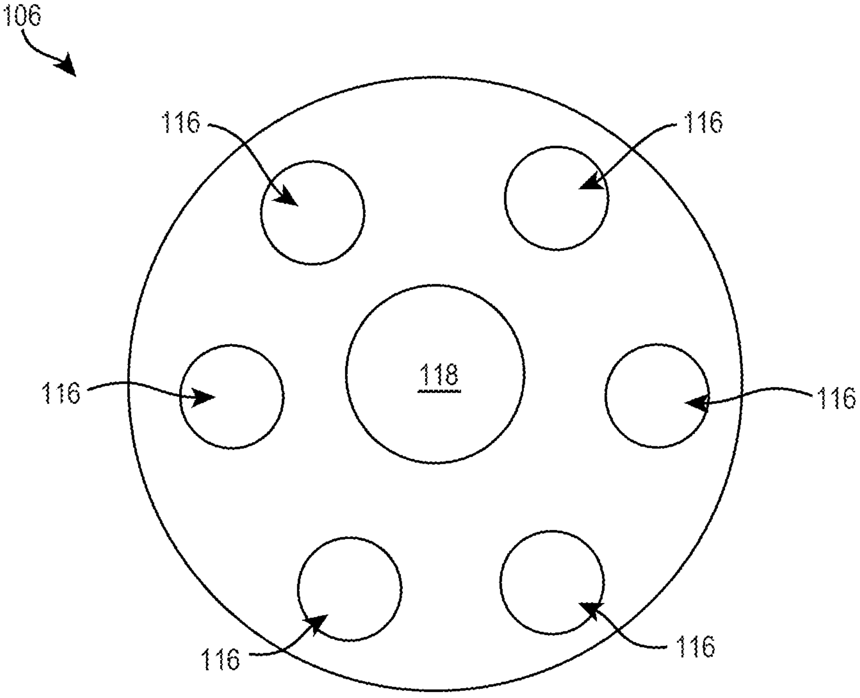

FIG. 15 is a top view of a coupler 106 for use with the treatment devices 100 of the present technology. The coupler 106 can be substantially identical to coupler 106 described with respect to FIG. 14, except coupler 106 does not include arm engaging elements in the first openings 116.

Figure 16:
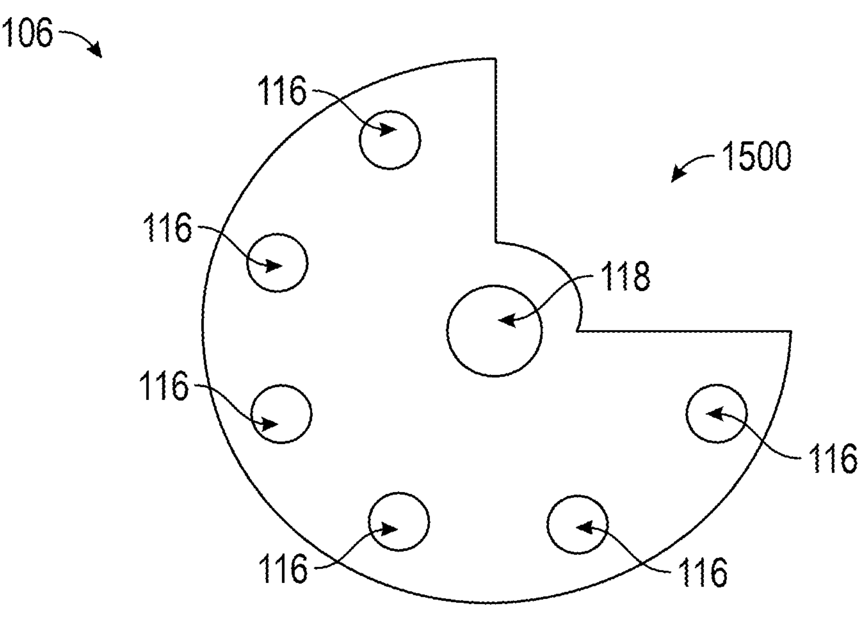

FIG. 16 is a top view of a coupler 106 for use with the treatment devices 100 of the present technology. The coupler 106 can be similar to the coupler 106 of FIG. 15, except the coupler 106 has a cut-out 1500 through which two or more arms 102 are configured to extend. Likewise, the coupler

Figure 17:
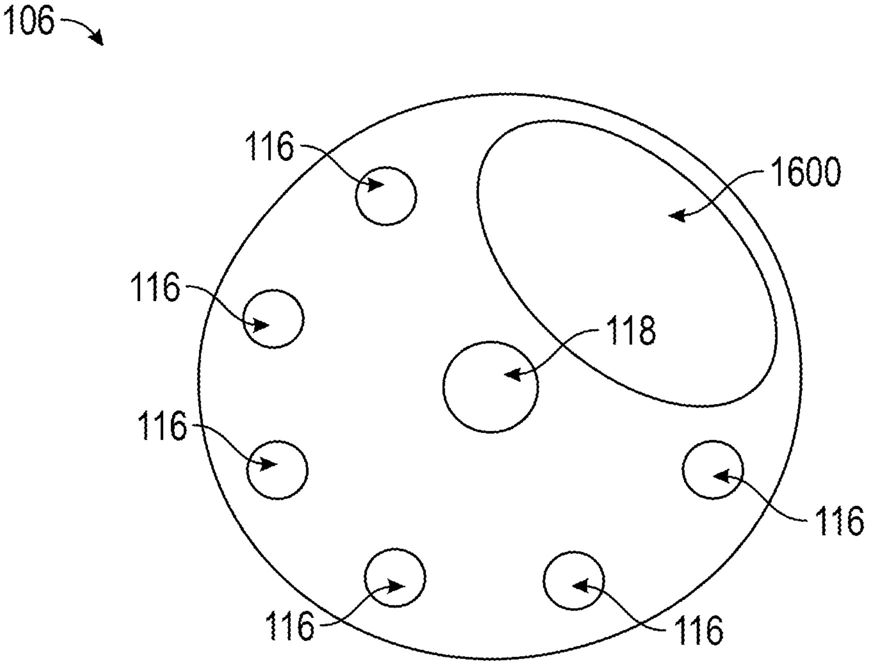

106 shown in FIG. 17 has an opening 1600 that is configured to receive two or more arms 102 therethrough. The couplers shown in FIGS. 16 and 17 can be beneficial as it allows movement of the coupler 106 without engaging at least some of the arms (i.e., the arms extending through cut-out 1500 or opening 1600). In some embodiments, one or more of the arms does not include any coupler engaging elements such that movement of the arms is decoupled from the movement of the coupler 106.

Figure 18:
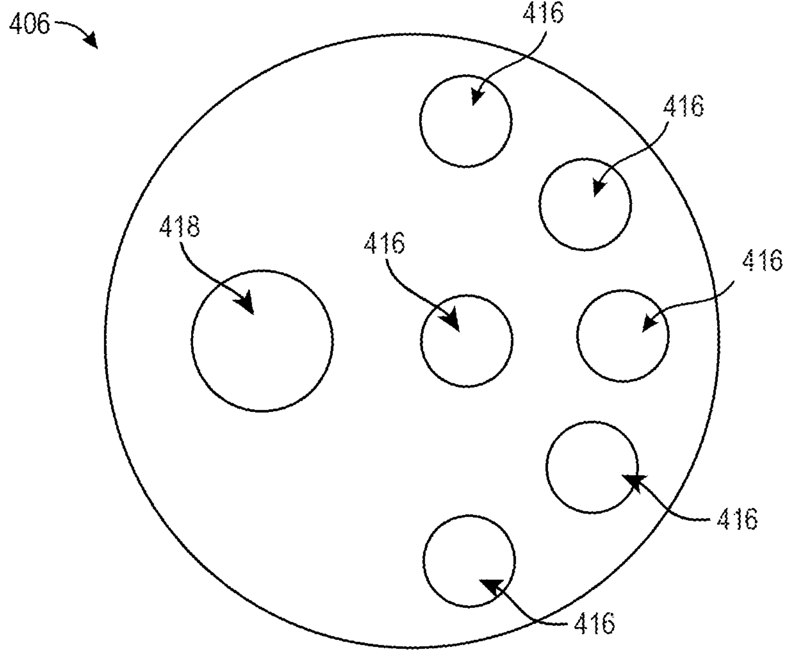
Figure 19:
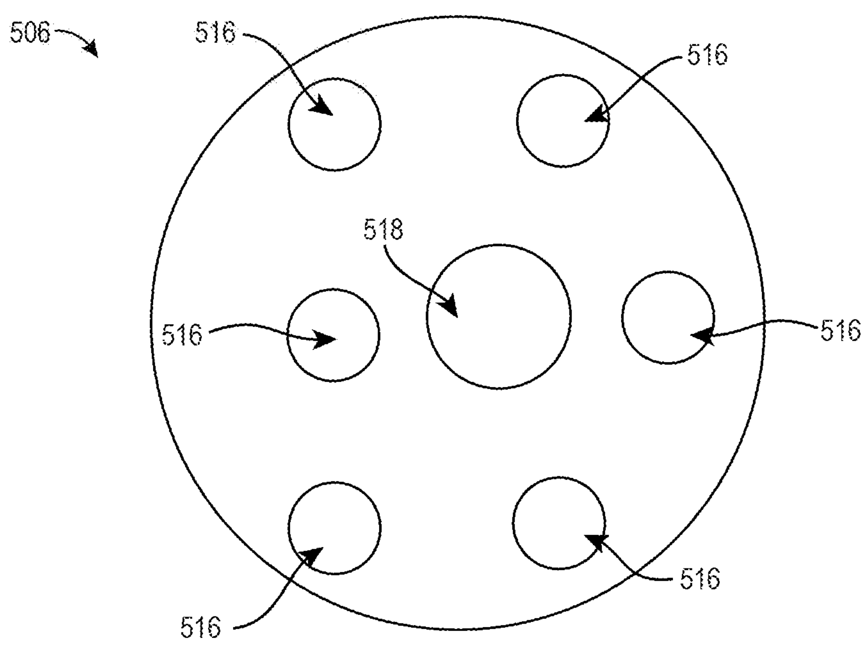

FIG. 18 is a top view of a coupler 406 for use with the treatment devices of the present technology. Similar to coupler 106, coupler 406 can comprise a disc having a plurality of openings extending therethrough. The plurality of openings can include one or more first openings 416 and one or more second openings 418. Each of the first openings 416 can be configured to receive one of the arms 102 therethrough. The second opening 418 can be configured to receive an end of the elongate structure for coupling the coupler 406 to a proximal portion of the system. In some embodiments, the coupler 406 can include additional openings. In contrast to the coupler 106 shown in FIGS. 5A and 5B, the second opening 418 of coupler 406 is positioned at one side of the disc, and the first openings 416 are disposed at the second side of the disc. In such embodiments, one or more of the arms 102 can be longer and/or have a greater curvature to compensate for the offset positioning at the coupler 106. Additionally or alternatively, the first openings 416 can be arranged in a D-shape, thereby orienting the arms 102 in a similar shape and mimicking the natural outline of the mitral valve annulus. In some embodiments, the first openings 416 can be arranged in other shapes or have other configurations. The second opening 418 can be positioned at any location along the area of the coupler. For example, the second opening 418 can be offset from the first openings 416 (as shown in FIG. 18) or may be positioned between the first openings 416 (for example as shown in FIGS. 5A and 19). In any case, the second opening may be sized to receive an imaging element (as described herein), the suture, a tool for locking and/or cutting the suture, and/or another component.

Figure 20:
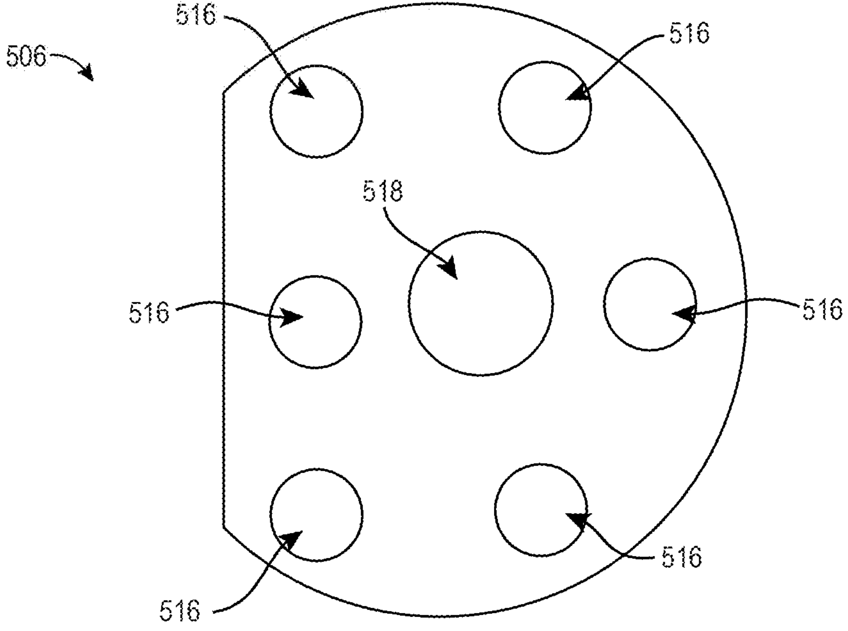

FIG. 19 shows an example coupler 506 configured in accordance with several embodiments of the present technology. The coupler 506 can be used with any of the devices disclosed herein. As shown in FIG. 19, in some embodiments the coupler 506 includes a plurality of first openings 516 arranged in a D-shape about the coupler 506, and a second opening 518 between and surrounded by the first openings 516. In these and in any of the coupler embodiments disclosed herein, the coupler 506 can have a non-circular shape. For example, in some embodiments the coupler 506 can have a D-shape, as shown in FIG. 20. In these and other embodiments a shape of the coupler can be a square, a rectangle, an ellipse, an oval, a triangle, a polygon, etc. and/or can have curved and/or linear edges. In the embodiments depicted by FIG. 20, the D-shaped coupler 506 has a D-shape and first openings arranged in a D-shape. In some embodiments, the D-shaped coupler 506 or any-shaped coupler described herein has openings in other arrangements, such as circular, rectangular, an ellipse, an oval, a triangle, a polygon, etc.

Figure 21:
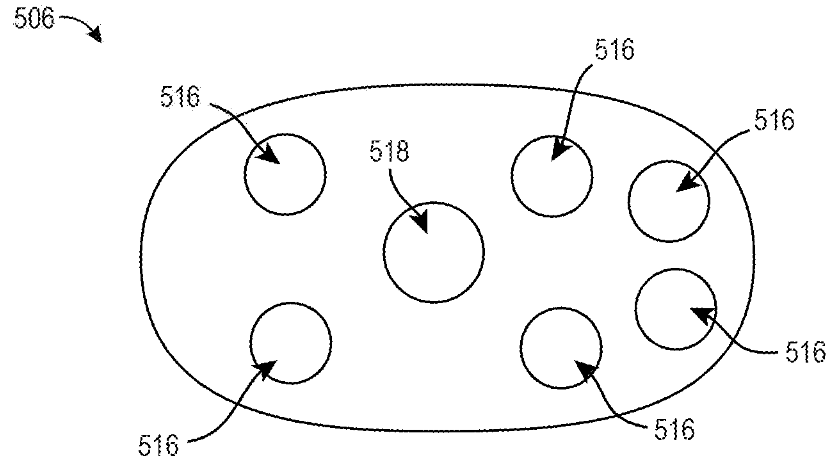

FIG. 21 shows an example coupler 506 configured in accordance with several embodiments of the present technology. The coupler 506 can be used with any of the devices disclosed herein. As shown in FIG. 21, in some embodiments the coupler 506 includes a plurality of first openings 516 arranged in a D-shape about the coupler 506, and a second opening 518 between and surrounded by the first openings 516.

Figure 22:
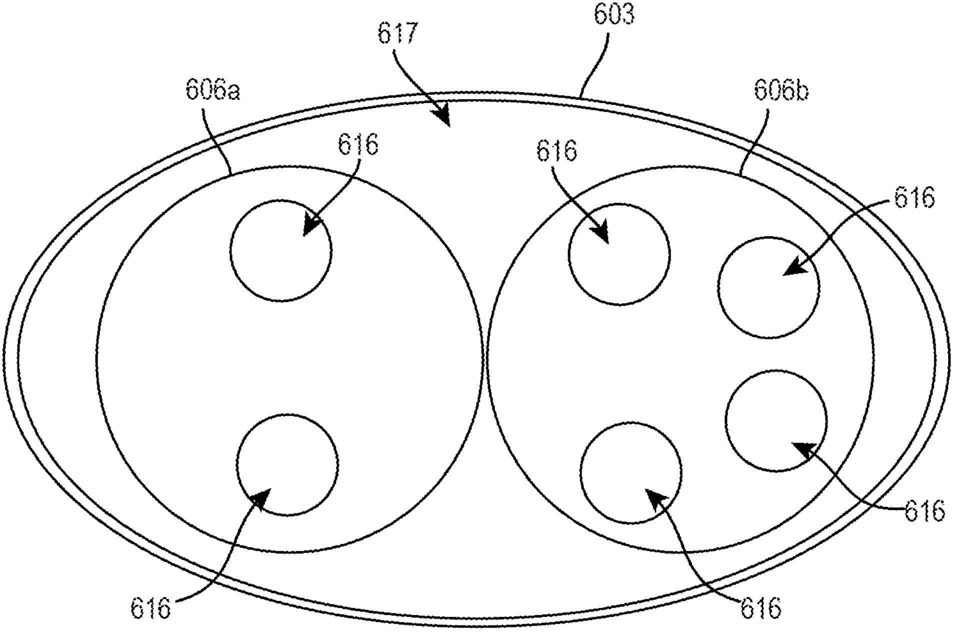

As shown in FIG. 22, in some embodiments the device 600 can include first and second couplers 606*a*, 606*b* configured to be arranged side-by-side in a delivery sheath 603. The first coupler and second couplers 606*a*, 606*b* can include one or more first openings 616, each configured to receive an arm 102 therethrough. The remaining space 617 in the lumen of the delivery sheath can be configured to receive a suture therethrough, an elongate structure, an imaging element, and/or other components. In some embodiments, one or both of the first and second coupler 606*a*, 606*b* have one or more second openings. The first and second couplers 606*a*, 606*b* can have the same number of openings or a different number of openings and/or the same or different shapes. In some embodiments, the first and second couplers can have other arrangements.

Figures 23A, 23B, 23C:
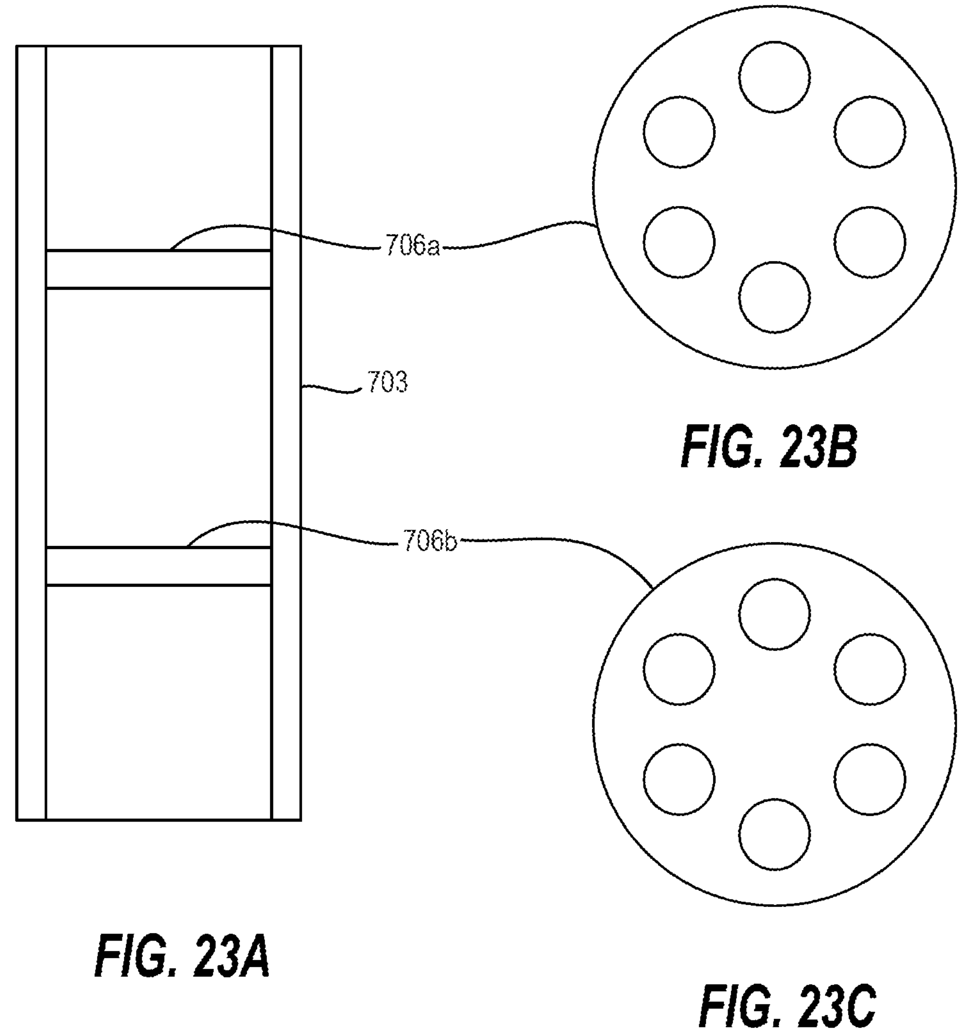

FIGS. 23A-23C depict a configuration in the which the device comprises first and second couplers 706*a*, 706*b* arranged colinearly in a delivery sheath 703. In FIG. 23A, a portion of the sidewall of delivery sheath 703 has been removed to show the first and second couplers. FIG. 23B is a top view of the first coupler 706*a* and FIG. 23C is a top view of the second coupler 706*b*. The first and second couplers 706*a*, 706*b* can have one or more first openings and one or more second openings, as shown schematically in FIGS. 23A-23C.

Figure 24B:
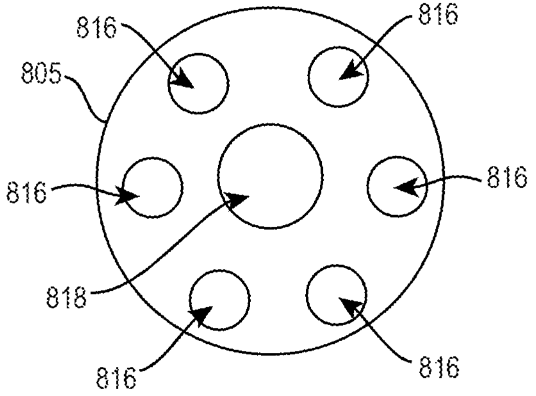
Figure 24A:
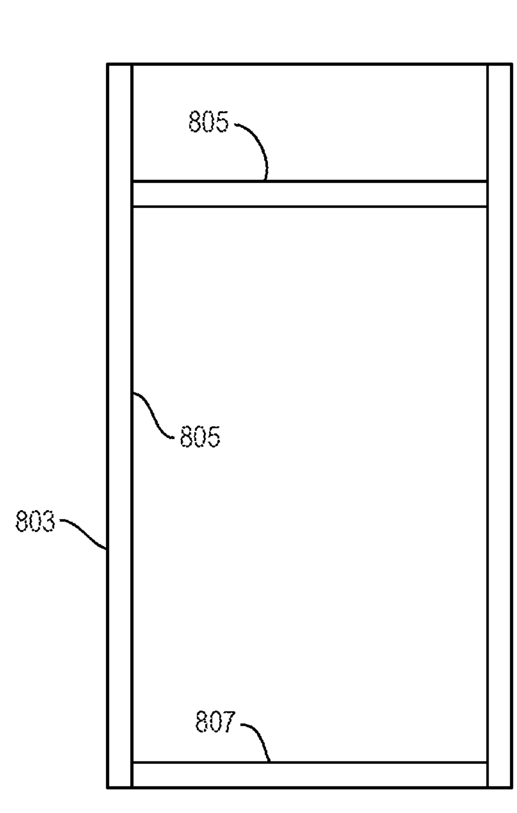
Figure 24C:
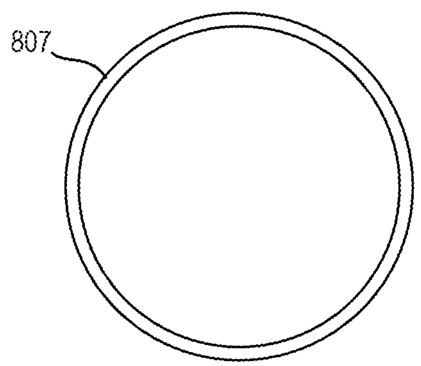

In some embodiments, the functions of the coupler may be split into two separate components. FIG. 24A, for example, shows a portion of a device having a positioning coupler 805 and a locking coupler 807, both disposed within a lumen of the delivery sheath 803. In FIG. 24A, a portion of the sidewall of delivery sheath 803 has been removed to show the couplers. FIG. 24B is a top view of the positioning coupler 805 and FIG. 24C is a top view of the locking coupler 807. Referring to FIGS. 24A-24C together, the positioning coupler 805 can have a plurality of openings (such as first openings 816 configured to receive the arms therethrough and one or more second openings 818) and is configured to hold the arms and/or elongate members spaced apart in a desired arrangement. The locking coupler 807 can be fixed to an inner surface 805 of the delivery sheath and can be rotated or moved axially to engage the locking elements along the arms. For example, the locking coupler 807 can be moved into alignment with the one or more grooves 112 on the arms to lock the arms in place. In some embodiments, instead of notches, the arms can have threads and the locking coupler 807 would then function like a nut and bolt arrangement, i.e., the locking coupler can be rotated relative to the arms (or vice versa) to move the locking coupler 807 distally relative to the arms, thereby pulling the arms together.

Figure 25B:
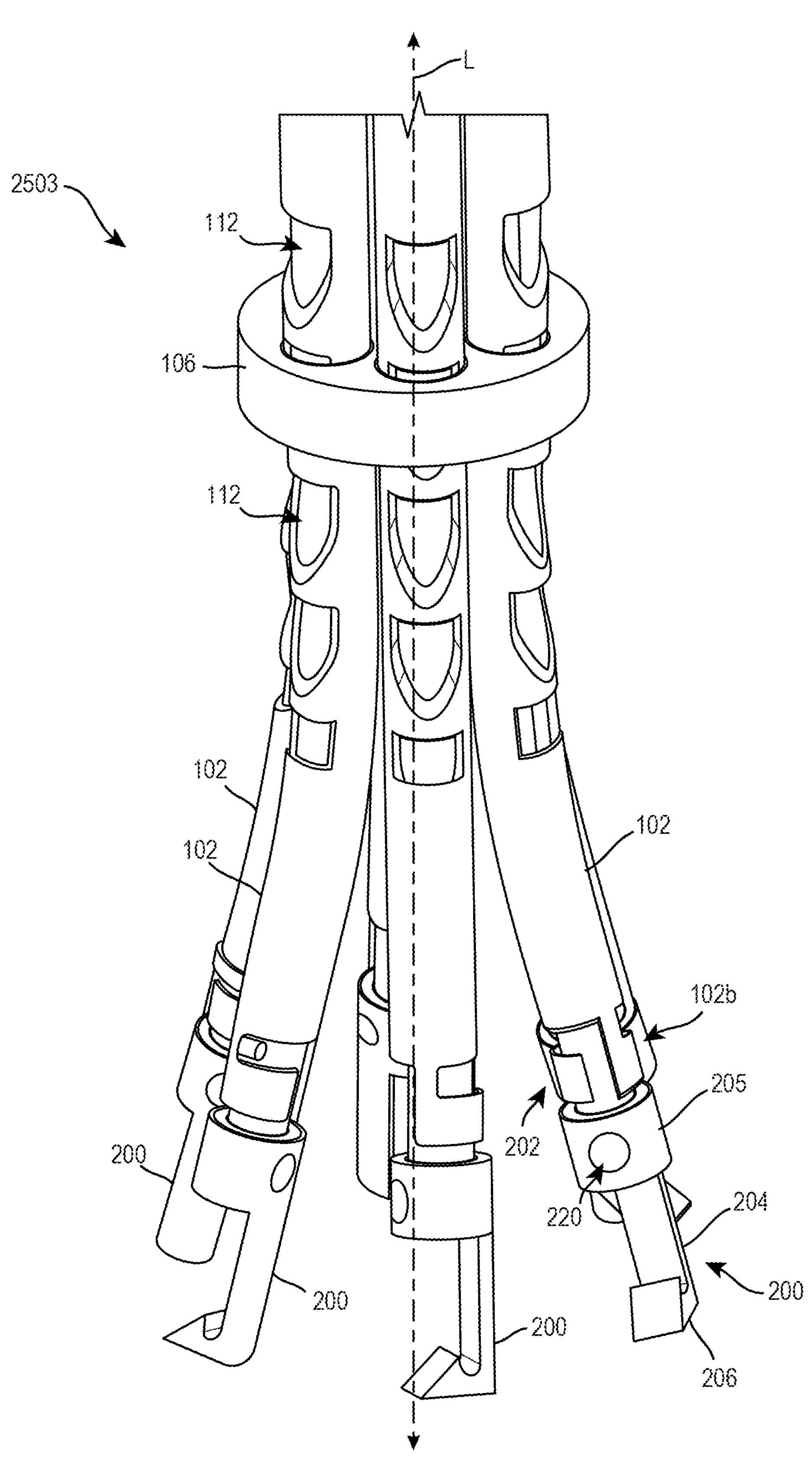

FIGS. 25A and 25B show a distal assembly 2503 configured in accordance with several embodiments of the present technology. The distal assembly 2503 can be generally similar to the distal assembly 103 of FIGS. 2A and 2B. For example, the distal assembly 103 includes arms 102 having coupler engaging elements 112, a coupler 106, elongate members 110, an elongated structure 105, bands 108, and a suture 114. The arms 102 can comprise hollow tubes such that the notches formed in the arms 102 expose the lumen of the arms 102.

A distal end portion 102*b* of each arm 102 can be detachably coupled to an anchor 200. In some embodiments, each of the anchors 200 may be detachably coupled to a corresponding one of the arms 102 such that, upon completion of treatment, the arms 102 may be removed from the patient (along with the rest of the device 100) while only the anchors 200 and suture 114 remain implanted at the annulus.

For example, the anchors 200 can be mechanically or electrolytically detachable from the distal portions 102*b* of the arms 102. In some embodiments, the handle includes an actuator that, when triggered by the operator, causes one, some, or all of the anchors 200 to release from a corresponding arm 102. For example, actuation of the release mechanism can cause a coupling element at the distal portion 102*b* of the arm 102 to disengage a coupling element at the coupling portion 202 of the anchor 200. In some embodiments, the distal portions of the arms 102 have a slot 107, and the proximal portions of the anchors 200 have a protrusion 203 that rides in that slot. To release the anchor, the corresponding arm 102 can be rotated relative to the anchor (or vice versa) so that the protrusion 203 on the anchor 200 becomes aligned with the exit path of the slot on the arm 102. When turning the arm 102 (clockwise or counterclockwise) to release the anchor 200, the operator can urge the arm 102 distally, towards the tissue, such that the anchor 200 is pushed further into the tissue and/or more surface area of the anchor contacts the tissue. As such, when the arm 102 is subsequently rotated, the tissue resists and/or prevents rotation of the anchor with the arm 102. Said more simply, the device may be configured such that a push and rotate motion (clockwise or counterclockwise) unlocks one, some, or all of the anchors 200 from the arms 102. In these and other embodiments, the arms 102 and anchors 200 may be coupled via a snap-fit assembly such that the anchor 200 snaps into the distal end of the arm 102. To disengage, another component can slide over the arm to help push the tabs on the anchor 200 back into the tube to release. Additionally or alternatively, the device may comprise one or more sutures or wires to hold the anchor to the corresponding arm. When the sutures or wires are pulled out of the handle, the anchors 200 detach as well.

Figure 25C:
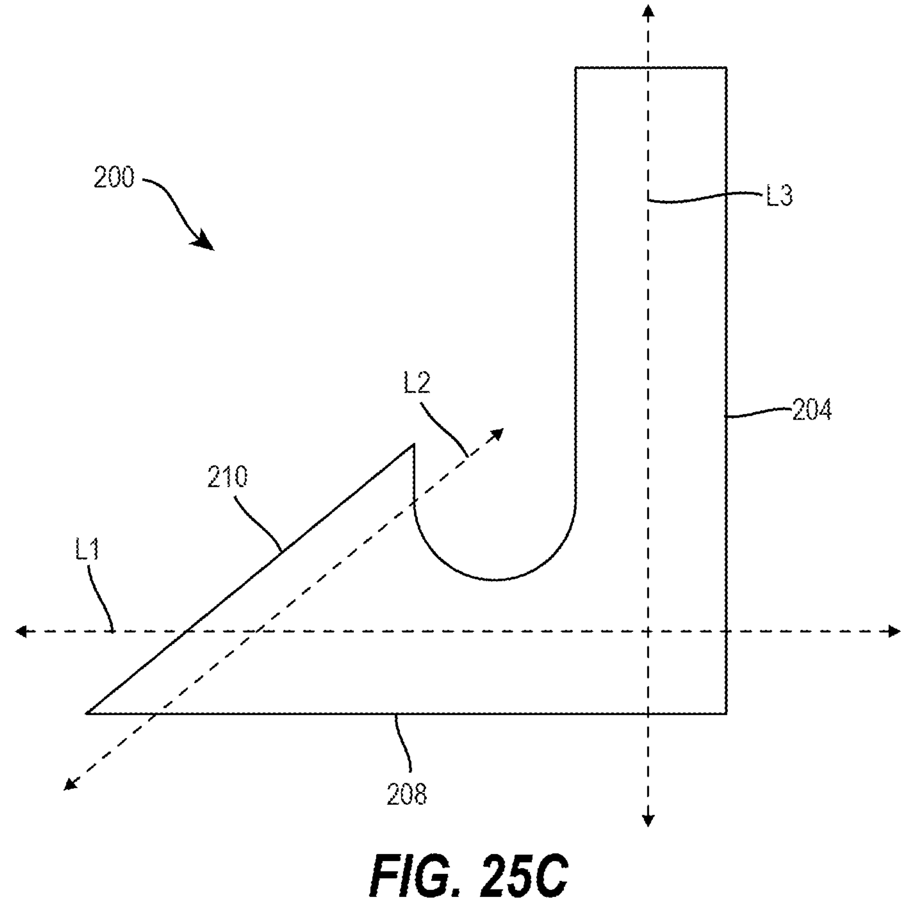
FIG. 25C is an enlarged view of an anchor of the distal assembly shown in FIGS. 25A and 25B.

Each of the anchors 200 can have a coupling portion 202 for detachably coupling to the corresponding arm 102, an intermediate portion 204 extending distally from the coupling portion 202, and a tissue engaging portion 206 extending laterally away from the intermediate portion 204. (Portions 202, 204 and 206 are only labeled on one of the anchors 200 in each of FIGS. 25A and 25B for ease of viewing the other components.) An enlarged view of the tissue engaging portion 206 of one of the anchors 200 is shown in FIG. 25C. The tissue engaging portion 206 can be configured to atraumatically or traumatically engage annular tissue to secure the anchor 200 to the tissue at a specific location. For example, the tissue engaging portion 206 can comprise one or more hooks, tines, barbs, or other fixation components. In some embodiments, the tissue engaging portion 206 includes a first region 208 extending laterally away from the intermediate portion 204 and a second region 210 extending laterally away from the first region 208. The longitudinal axis L3 of the intermediate region 204 can be positioned at a 90 degree angle relative to the longitudinal axis L1 of the first region 208 (as shown in FIG. 25C), or the longitudinal axis L3 can be positioned at a non-90 degree angle relative to the longitudinal axis L1 of the first region 208. The angle between the intermediate region 204 and the second region 208 can be adjusted based on the desired tissue engaging properties. For example, the closer the angle between the intermediate region 204 and the second region 208 is to 90 degrees, the more difficult it will be to remove the anchor from the tissue. The longitudinal axis L2 of the second region 210 can be positioned at a non-90 degree angle relative to the longitudinal axis L1 of the first region 208. The angle between the first and second regions 208, 210 can be adjusted based on the desired tissue engaging properties. In some embodiments, one, some, or all of the anchors 200 can be retractable by advancing and/or rotating the corresponding arm 102.

In use, the device 100 can be intravascularly positioned at or proximate a native valve annulus, such as a heart valve annulus, with the arms 102 contained in a delivery sheath in a low-profile delivery configuration. In some embodiments, the arms 102 can be released from the constraints of the delivery sheath by pushing the arms 102 through the opening at the distal end of the elongated shaft 120. For example, as previously discussed, the coupler 106 can be advanced distally until it engages a proximal portion of the arms 102, at which point continued axial advancement of the coupler 106 also advances the arms 102 (so long as the arms are not fixed axially by one or more actuators, as discussed above). In some embodiments, the elongated shaft 120 can be pulled proximally to expose the arms 102, thereby allowing the arms 102 to extend radially away from the longitudinal axis L of the device 100 into a deployed configuration. In any case, the device 100 can be deployed proximate to and above the annulus such that the anchor assemblies 122 are positioned proximate the annular tissue just above the plane of the valve orifice.

As the arms 102 extend away from the longitudinal axis L of the device 100, the anchors 200 also move radially away from the longitudinal axis L of the device 100 towards annular tissue within or just above the plane of the orifice. The expansion force associated with the initial deployment of the arms 102 can bring the anchors 200 into contact with annular tissue. In some embodiments, the entire device 100 can be rotated about the longitudinal axis L so that the tissue engaging portions 206 of the anchors 200 penetrate or further penetrate annular tissue. Each one of the arms 102 can be independently rotated and/or translated as needed to position each anchor 200 at a desired anchor point along the native annulus. Independent movement of the arms 102 enables independent movement of the anchors 200, thereby allowing the device 100 to treat a wide variety of annulus shapes and sizes. Once the anchors 200 are in a desired position relative to the annular tissue, one or more components of the device 100 can be actuated to move the anchors 200 into contact with the annular tissue. For example, in some embodiments, axial movement and/or rotation of the coupler 106 rotates all of the arms 102 simultaneously such that the anchors 200 engage and/or embed within the tissue at substantially the same time, thereby saving procedural time. In some embodiments, one or more of the arms 102 can be translated and/or rotated to partially or completely remove the anchors 200 from the tissue.

The operator can then actuate the detachment mechanism from the handle to detach the anchors 200 from the corresponding arms 102, thereby leaving the anchors 102 implanted at the annulus. The arms 102, coupler 106, elongate members 110, and the rest of the device 100 is then withdrawn from the patient.

Figure 26:
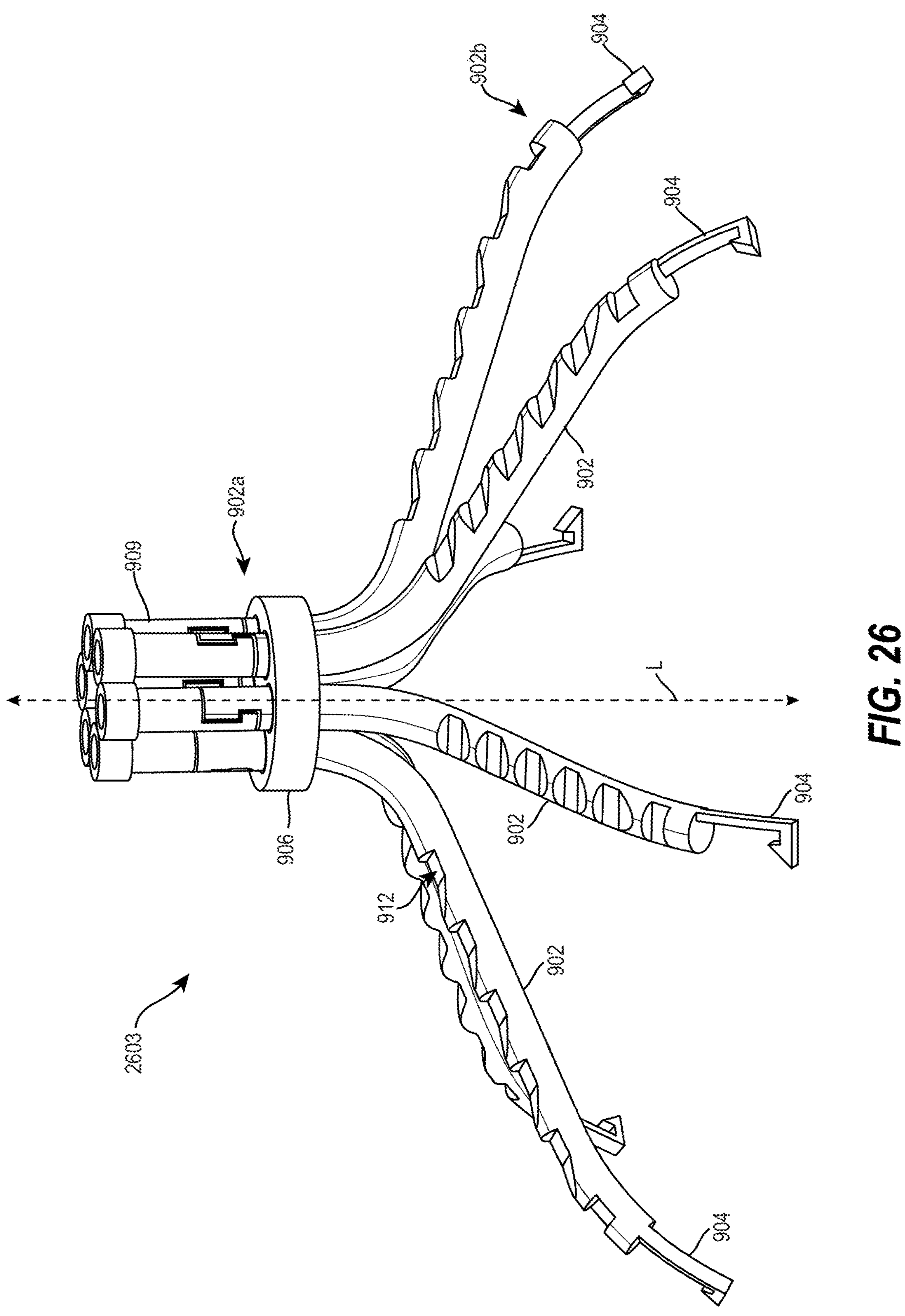
FIG. 26 illustrates a distal assembly configured in accordance with several embodiments of the present technology.

FIG. 26 shows a distal portion of a distal assembly 2603 for treating native cardiac valves configured in accordance with several embodiments of the present technology. The distal assembly 2603 of FIG. 26 can have some components substantially similar to the components of the distal assembly 2503 of FIGS. 25A and 25B. In contrast to distal assembly 2503, however, distal assembly 2603 includes anchors 904 that are non-detachable from the arms 902. For example, the anchors 904 can be part of the same, monolithic piece of material as the arms 902. In the embodiment shown in FIG. 26, the arms 902 and anchors 904 are cut from a single metal tube (e.g., a nitinol tube or other superelastic and/or resilient material). In some embodiments, the anchors 904 and arms 902 may be formed separately and attached permanently together, e.g. by welding, etc.

In those embodiments in which the arms and anchors are permanently fixed to one another, the arms may be detachably coupled to the elongate members and left implanted at the annulus with the anchors. For example, each of the proximal end portions 902*a* of the arms 902 can be releasably coupled to the distal end portions of the elongate members (not shown in FIG. 26) via coupling members 909. In some embodiments, for example as shown in FIG. 26, the proximal end of the arm is an L-shaped piece that fits into another component that is also L-shaped. That component can be crimped onto a braided wire so it acts as one piece. The device can include a separate tube that goes over the two L-shaped ends to keep the two pieces together. When the tube is pulled back, it allows the two L-shaped ends to separate, therefore leaving the arms and coupler behind in the patient. A snap-fit assembly, locking arrangements, and other configurations and coupling elements are also possible. For example, the component can be glued or even manufactured from one piece of metal tube (laser cut on the back end and the front end of the tube form the L-shape connection). In these and other embodiments, each of the proximal end portions 902*a* of the arms 902 can be detachably coupled to the distal end portions of the elongate members via a mechanical or electrolytic detachment means.

Figure 27:
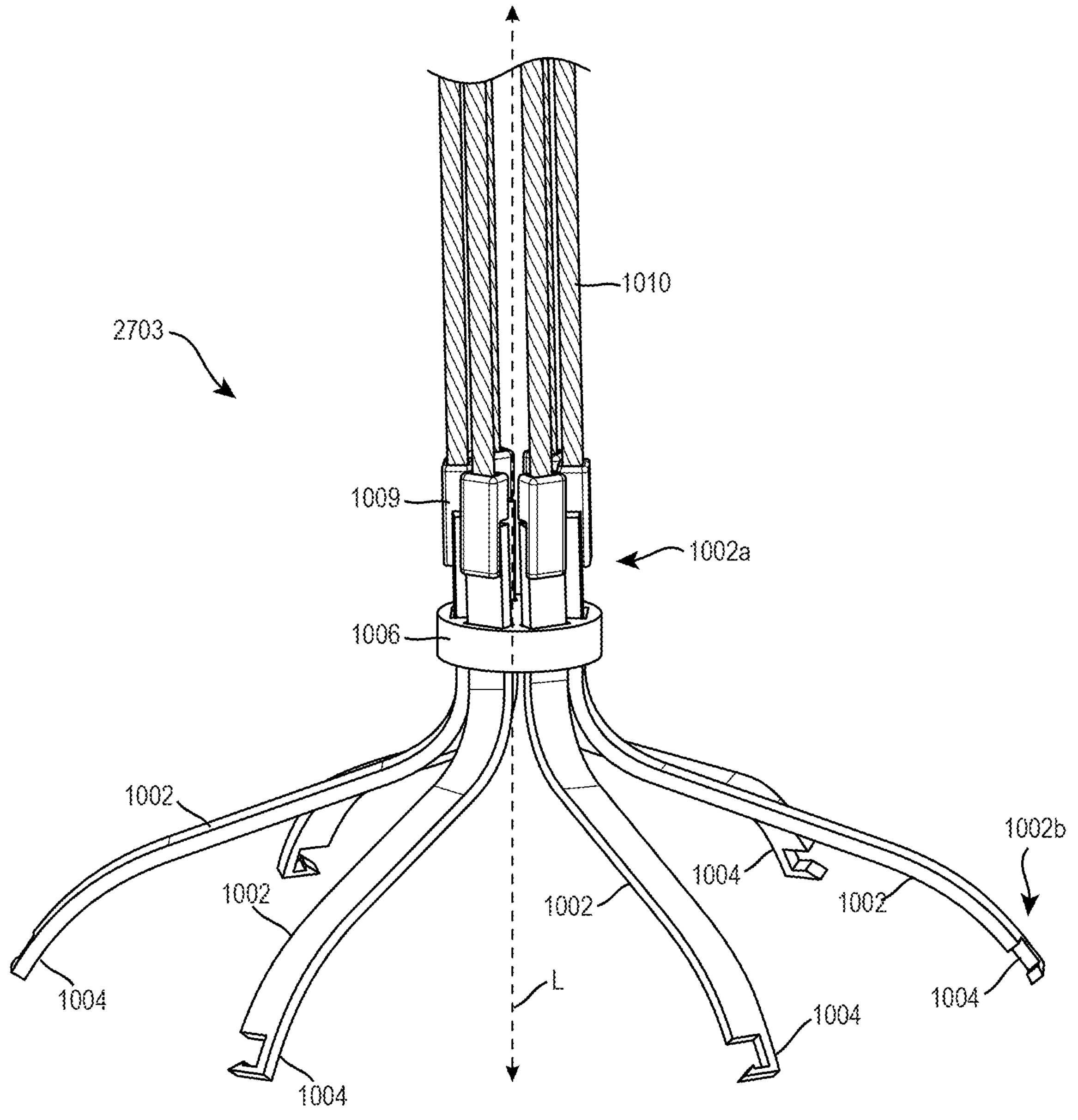
FIG. 27 illustrates a distal assembly configured in accordance with several embodiments of the present technology.

FIG. 27 shows a distal portion of a distal assembly 2703 for treating native cardiac valves configured in accordance with several embodiments of the present technology. The distal assembly 2703 of FIG. 27 can have some components substantially similar to the components of the distal assembly 2503 of FIG. 25A. In contrast to distal assembly 2503, however, distal assembly 2703 includes anchors 1004 that are non-detachable from the arms 1002. For example, the anchors 1004 can be part of the same, monolithic piece of material as the arms 1002. In the embodiment shown in FIG. 27, the arms 1002 and anchors 1004 are cut from a flat metal ribbon (e.g., a nitinol tube or other superelastic and/or resilient material). In some embodiments, the anchors 1004 and arms 1002 may be formed separately and attached permanently together, e.g. by welding, etc. The proximal end portions 1002*a* of each of the arms 1002 can be releasably coupled to the distal end portions of the elongate members 1010 via couplers 1009. For example, the coupler 1009 can be a clip, and the proximal end portions 1002*a* of each of the arms 1002 can include an opening configured to receive a portion of the clip. The device may further comprise a securing member (such as a tube or other component) configured to be positioned over the clip and that holds the clip in the locked position (not shown). Once the securing member is pulled away from the clip, the clip is free to open and release the corresponding arm. In these and other embodiments, each of the proximal end portions 1002*a* of the arms 1002 can be detachably coupled to the distal end portions of the elongate members 1010 via a mechanical or electrolytic detachment means.

Figure 28A:
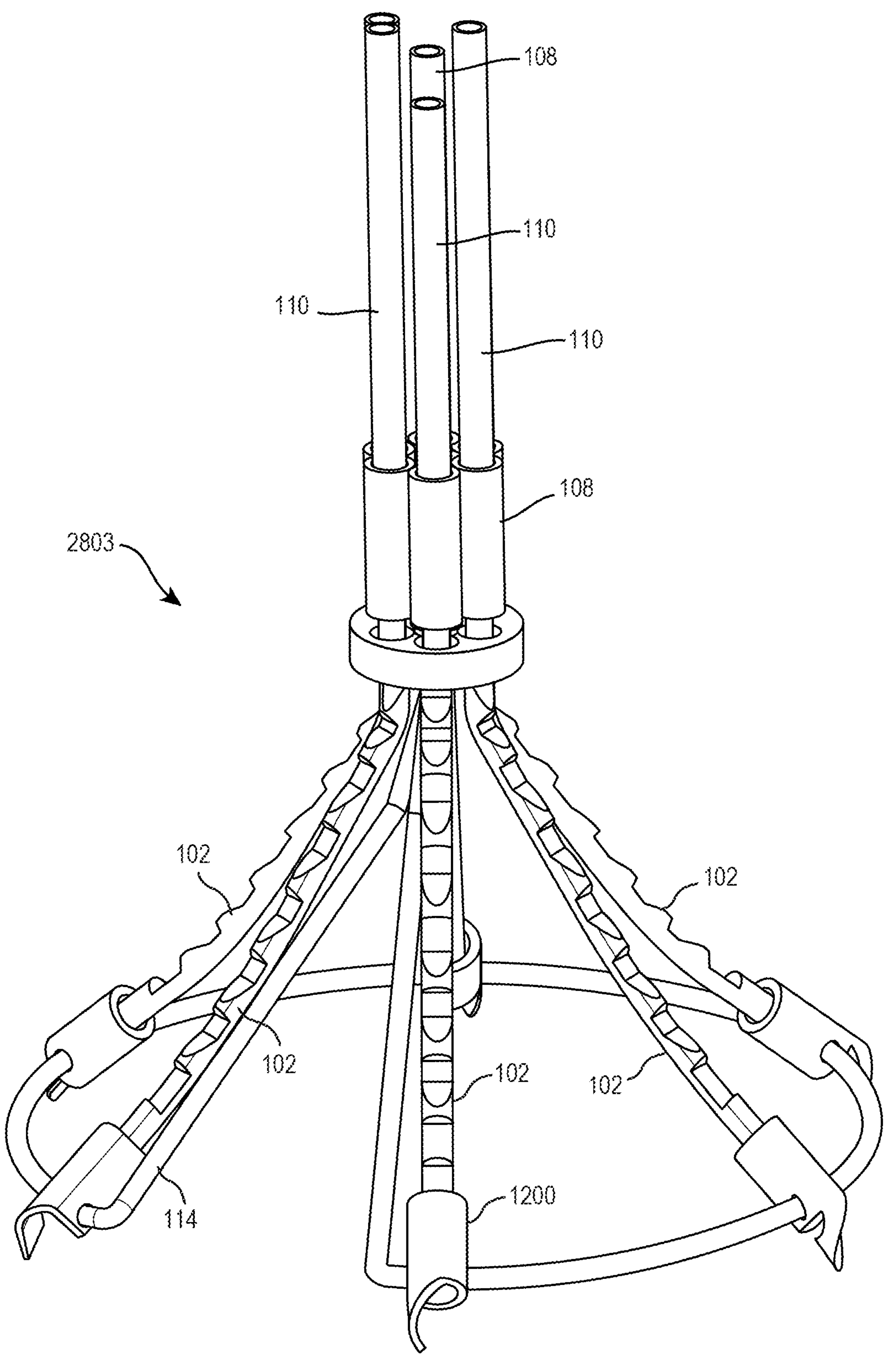
FIG. 28A illustrates a distal assembly configured accordance with several embodiments of the present technology.
Figure 28B:
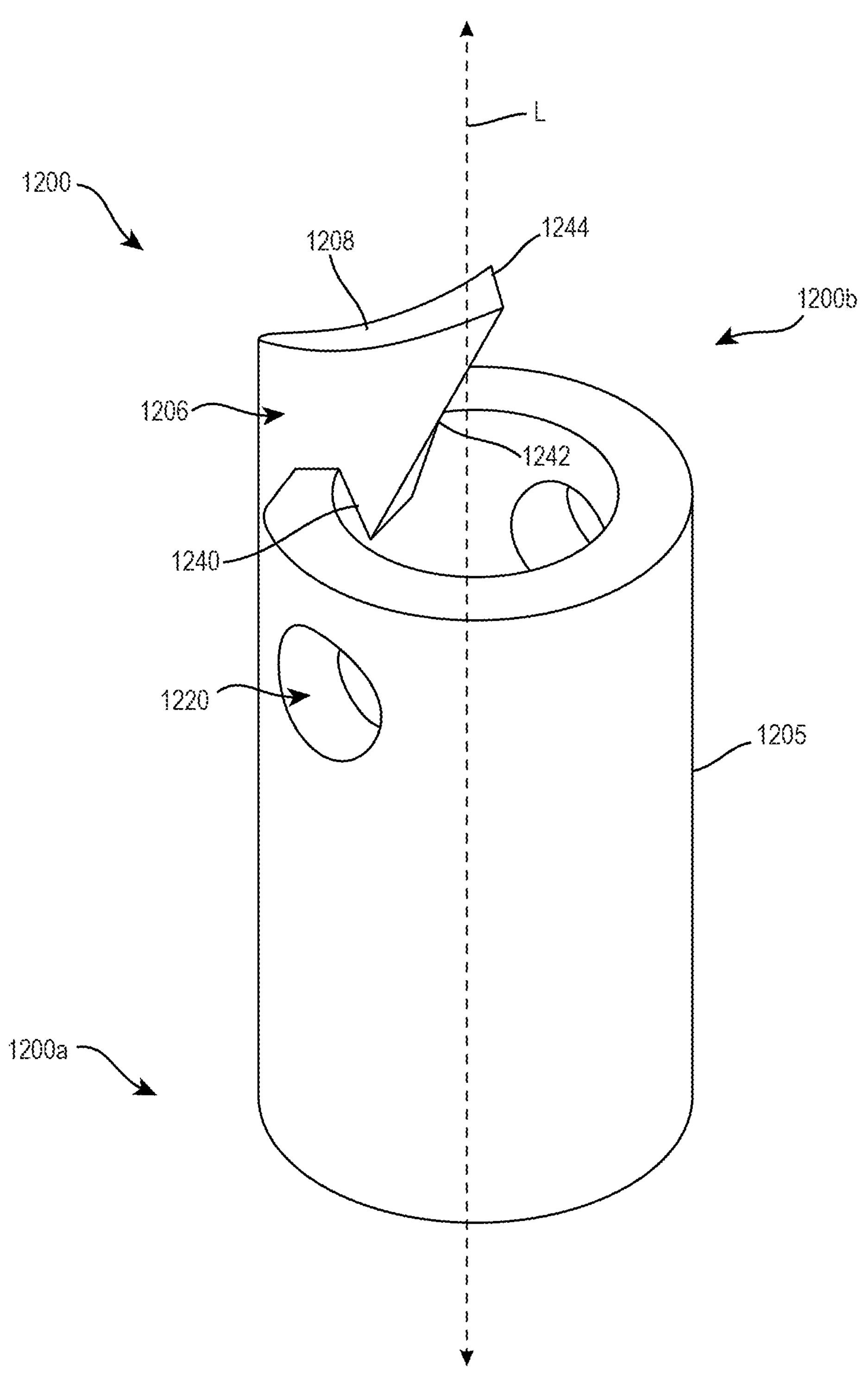
FIG. 28B is an enlarged view of an anchor of the distal assembly shown in FIG. 28A.

FIG. 28A shows a distal assembly 2803 in a first position in accordance with several embodiments of the present technology. FIG. 28B is an enlarged view of an anchor of the device shown in FIG. 28A. The distal assembly 2803 of FIG. 28A can be generally similar to the distal assembly 2503 of FIGS. 25A and 25B, except the anchors 1200 shown in FIGS. 28A and 28B comprise a curved tissue engaging portion, as described below. The anchor 1200 can be formed from the same tube for the arms (e.g., via laser drilling, CNC, EDM, etc.), or may be a separate component detachably coupled to the arms.

The anchor 1200 can have a proximal portion 1200*a*, a distal portion 1200*b*, and a longitudinal axis L extending therebetween. The proximal portion 1200*a* can include a coupling portion for detachably coupling to the corresponding arm 102, and the anchor 1200 can further include an intermediate portion 1205 coinciding with or extending distally from the coupling portion 1200*a*. The intermediate portion 1205 can include one or more openings 1205 configured to receive a suture therethrough.

The anchor 1200 can further include a tissue engaging portion 1206 extending away from the intermediate portion 1205. The tissue engaging portion 1206 can be configured to atraumatically or traumatically engage annular tissue to secure the anchor 1200 to the tissue at a specific location. For example, the tissue engaging portion 1206 can comprise one or more hooks, tines, barbs, or other fixation components. In some embodiments, the tissue engaging portion 1206 extends longitudinally away from the intermediate portion 1205 at an angle while simultaneously curving about the longitudinal axis L of the anchor 1200. The tissue engaging portion 1206, for example, can curve around about 10%, 20%, 30%, 40%, 50%, 60%, 70%, 80%, 90% or greater than 100% of a circumference of the anchor 1200. The tissue engaging portion 1206 can have a radius of curvature that is greater than or less than a radius of curvature of the intermediate portion 1205. Similarly, the tissue engaging portion 1206 can extend radially beyond a radially outermost portion of the intermediate portion 1205. The tissue engaging portion 1206 include a curved, distal-facing side 1208, a leading edge 1244 (which could be traumatic or atraumatic) that extends distally from the rest of the tissue engaging portion 1206, a proximally-facing side 1242, and a proximally-extending protrusion 1240. To lock the anchor into the tissue, the arm can be rotated less than a full, 360 degree turn. For example, to lock the anchor into the tissue, the arm can be rotated less than 270 degrees, less than 180 degrees, less than 135 degrees, less than 90 degrees, less than 45 degrees, less than 30 degrees, less than 20 degrees, less than 15 degrees, less than 10 degrees, less than 5 degrees, between 10 and 90 degrees, between 20 and 180 degrees, between 45 and 180 degrees, etc. In some embodiments, the arm can be rotated a full turn or more (1.25 turns, 1.5 turns, 1.75 turns, 2 turns, etc.).

The anchor 1200 can be detached from a corresponding arm via any of the releasing mechanisms disclosed herein.

Figure 29:
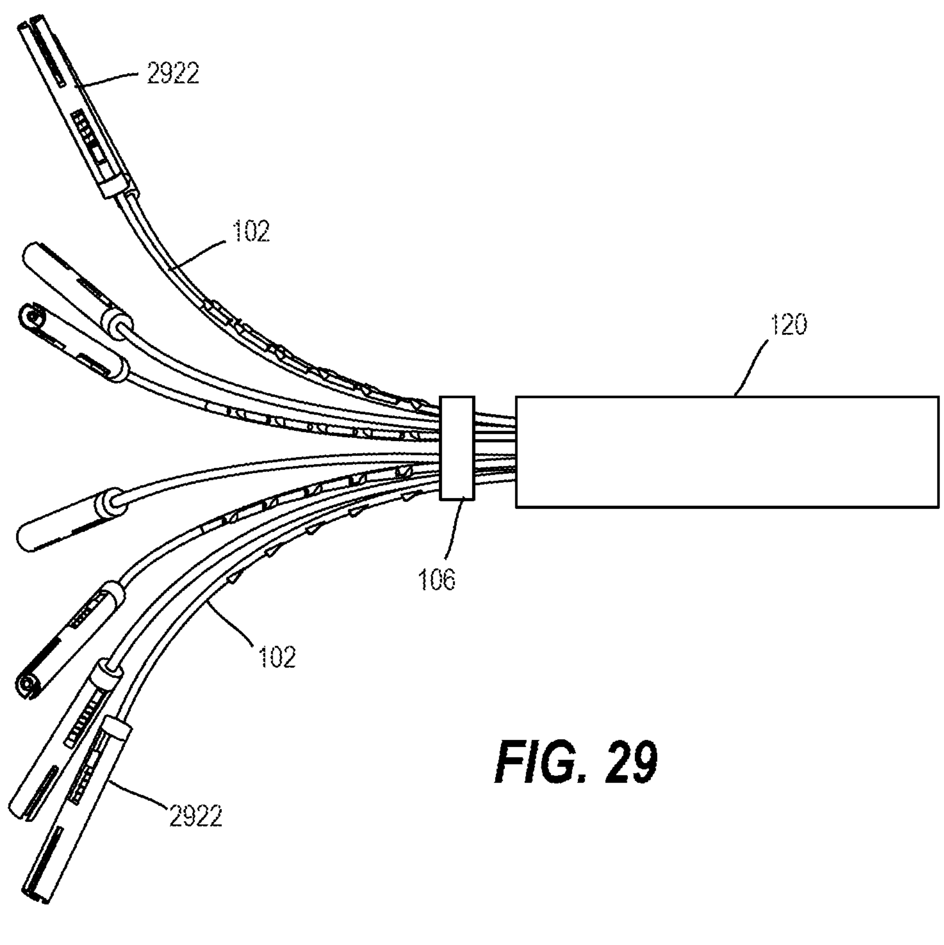
FIGS. 29 and 30 are perspective and cross-sectional views, respectively, of an anchor assembly configured for use with the treatment devices of the present technology.
Figure 30:
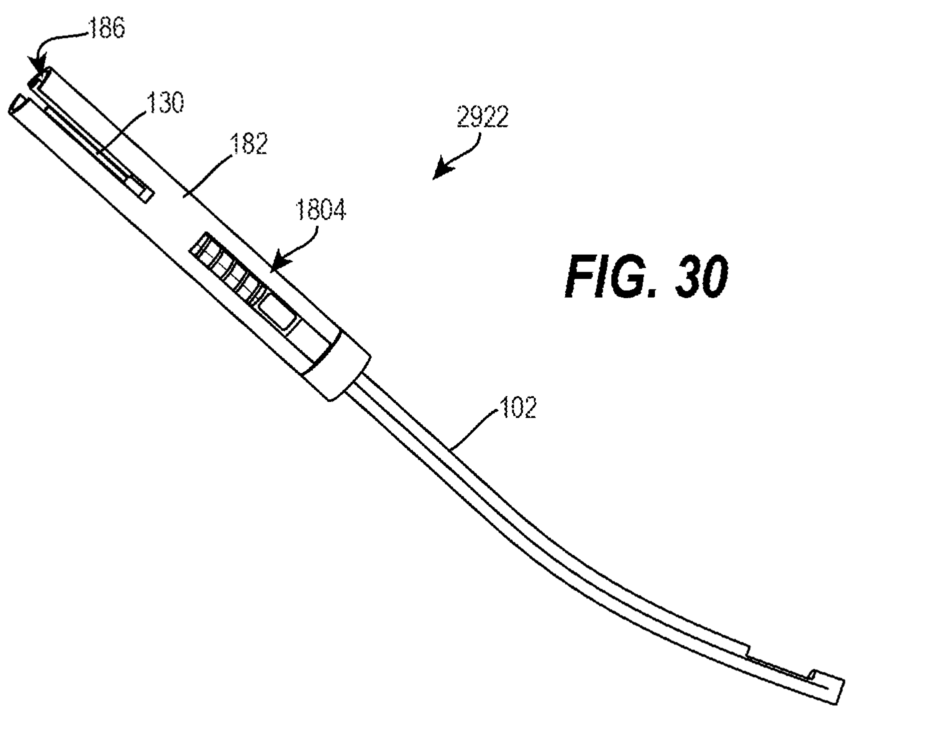
Figures 31A, 31B, 31C, 31D:
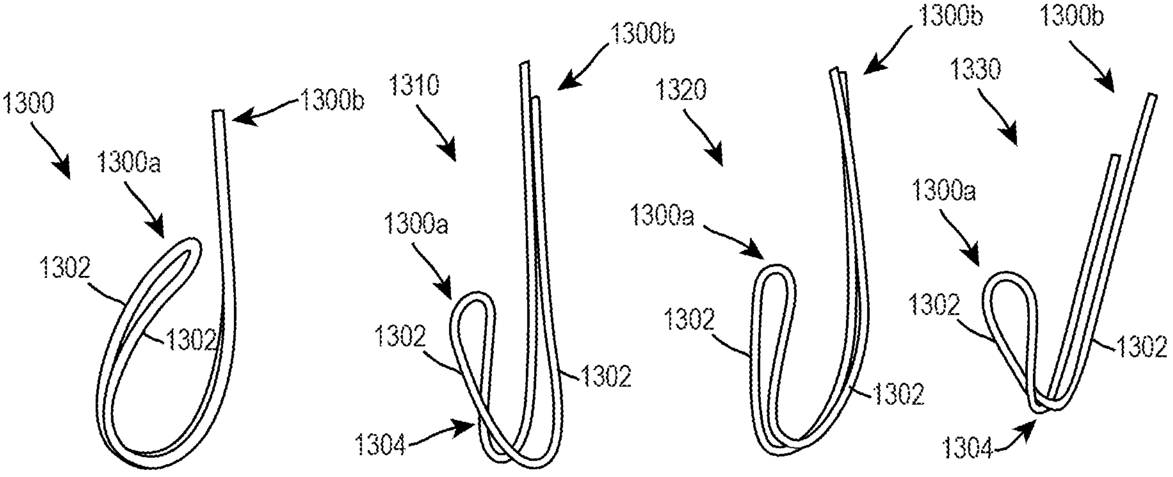
FIGS. 31A-31G show different anchors configured in accordance with several embodiments of the present technology.
Figures 31E, 31F, 31G:
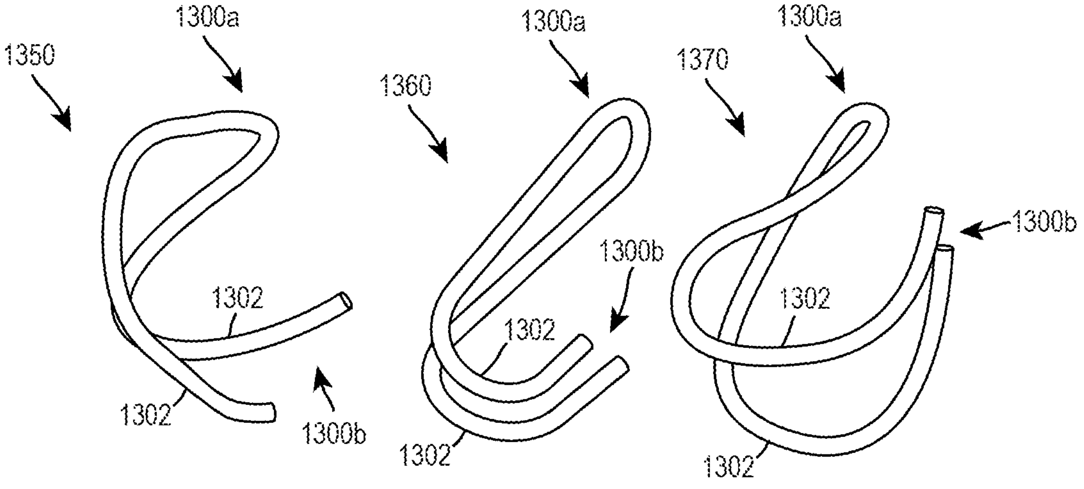

FIGS. 29 and 30 are perspective and cross-sectional views of an anchor assembly 2922. The anchor assembly 2922 can be configured to deploy a corresponding anchor 130 into the tissue in response to an axial force above a predetermined threshold, thereby preventing accidental deployment of the anchor from the delivery system. As shown in the enlarged view of FIG. 18, the anchor assembly 122 can comprise a housing 1802 and a spring-loaded pusher 1804 carried by the housing 1802. The housing 1802 can be configured to contain the anchor until deployment is desired. In use, the physician pushes the corresponding arm 102 distally to place the distal end surface 1806 of the housing 1802 into contact with the tissue at a desired fixation site. The physician can continue to press the distal end of the housing 1802 against the tissue which eventually triggers the spring-loaded pusher that forcefully ejects the anchor from the housing 1802 into the tissue.

In some embodiments, the device includes one or more elongated members (a wire, a tube, etc.) having a distal end coupled to the anchor and a proximal end coupled to the handle. If the physician is not happy with the deployment, the physician can pull back on the wire to pull the anchor proximally out of the tissue and back into the housing 1802. For any of the anchors discussed herein with reference to FIGS. 9 and 31A-35, withdrawal of the anchors into the housing 1802 straightens the bend of the anchors and forces the anchors into a radially collapsed profile that fits within the lumen of the housing 1802.

FIGS. 31A-35 illustrate various anchors of the present technology comprising multiple insertion arms. The use of multiple insertion arms may provide improved penetration and gripping of the annular tissue relative to a single insertion arm.

FIGS. 31A-31G shows a variety of anchor designs 1300, 1310, 1320, 1330, 1350, 1360, 1370 (referred to collectively as "anchors 1340"), each comprising a proximal end portion 1300*a* configured to be detachably coupled to a component of the delivery system and a distal end portion 1300*b* configured to penetrate and be embedded in annular tissue. The anchors 1340 can be formed of an elongated member, such as a wire, that is bent back on itself to form two arms 1302. The proximal ends of the arms 1302 are thus joined at the bend, and the distal ends correspond to the distal end portion 1300*b* of the anchor 1300. In some embodiments, the distal ends are beveled to provide a sharpened surface for penetrating the annular tissue. In other embodiments, the distal ends are blunt. A suture can be threaded through the opening formed by the bend in the elongated member at the proximal end portion 1300*a* of the respective anchor.

The elongated member of the anchors 1340 shown in FIGS. 31A-31G comprise a wire having a round cross-sectional shape. In other embodiments, the elongated member and/or wire forming the anchors 1340 can have any suitable cross-sectional shape. For example, in some embodiments the elongated member comprises a wire having a rectangular cross-sectional shape. The elongated member can be formed of a superelastic and/or resilient material, such as nitinol, cobalt chromium, and/or alloys thereof. In such embodiments, the elongated member can be shape set such in a desired shape (e.g., via a heat treatment).

In some embodiments, the arms 1302 do not cross between the proximal and distal end portions 1300*a*, 1300*b* of the anchor, for example as depicted by anchors 1300 and 1320. In other embodiments the arms 1302 cross over one another between the proximal and distal end portions 1300*a*, 1300*b*, for example as depicted by anchors 1310 and 1330. The intersection 1304 between the arms 1302 can provide additional structural support to the tissue-engaging portion of the anchor, thereby improving fixation with the tissue.

Figure 32A:
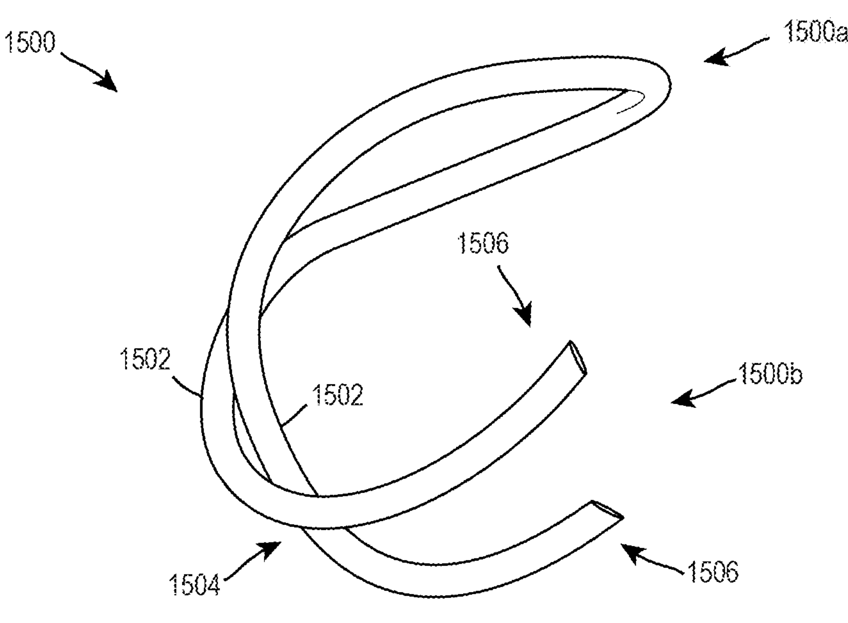
FIGS. 32A and 32B are different views of an anchor configured in accordance with several embodiments of the present technology.
Figure 32B:
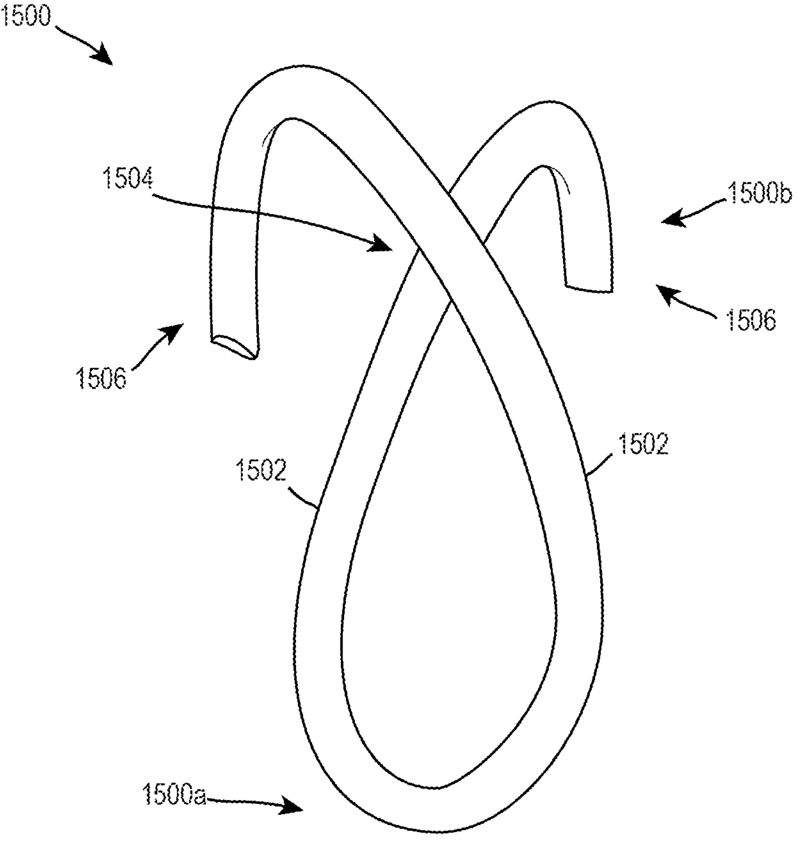

FIGS. 32A and 32B are different views of another example of an anchor 1500 in accordance with embodiments of the present technology. The features of the anchor 1500 can be generally similar to the corresponding features of the anchors 1340 of FIGS. 31A-31G. Accordingly, like numbers are used to identify similar or identical components in FIGS. 32A and 32B. In any of the anchor embodiments herein, the location of the intersection of the arms can affect the grip strength of the anchors.

FIGS. 33, 34 and 35 illustrate additional examples of anchors 1600, 1600', and 1600" in accordance with embodiments of the present technology. The features of the anchors 1600, 1600', and 1600" can be generally similar to the corresponding features of the anchors of FIGS. 31A-31G. Accordingly, like numbers are used to identify similar or identical components in FIGS. 33-35, and the discussion of the anchors 1600, 1600', and 1600" of FIGS. 33-35 will be limited to those features that differ from the anchors of FIGS. 31A-31G.

In contrast to the bent elongated members of FIGS. 9 and 31A-32B, the anchors 1600, 1600', and 1600" shown in FIGS. 33-35 are formed of a laser cut sheet of material that is subsequently bent into a desired shape (via a shape set, cold working, or other suitable method). The anchors 1600, 1600', and 1600" further comprise an opening 1608 extending through a thickness of the material and through which a suture may be threaded. All or a portion of the outer surfaces of the arms 1602 can be flat, which may provide improved engagement with the tissue (relative to a rounded surface).

Any of anchors 1600, 1600', and 1600" can be used with the anchor assemblies 122 and 2922 and any of the distal assemblies disclosed herein, including distal assembly 103.

For any of the anchor embodiments described herein, including those shown in FIGS. 31A-35, the anchor can have a single arm or more than two arms (e.g., three arms, four arms, five arms, etc.). In those embodiments in which the anchor comprises a single arm, the arm may be thicker than an individual arm of a two-arm embodiment. For example, for the anchors shown in FIGS. 31A-35, the elongated member can have a greater cross-sectional dimension. In the embodiments exemplified by FIGS. 33-35, a single-armed anchor can have an arm with a thickness greater than a thickness of either of the arms 1602.

Figure 36:
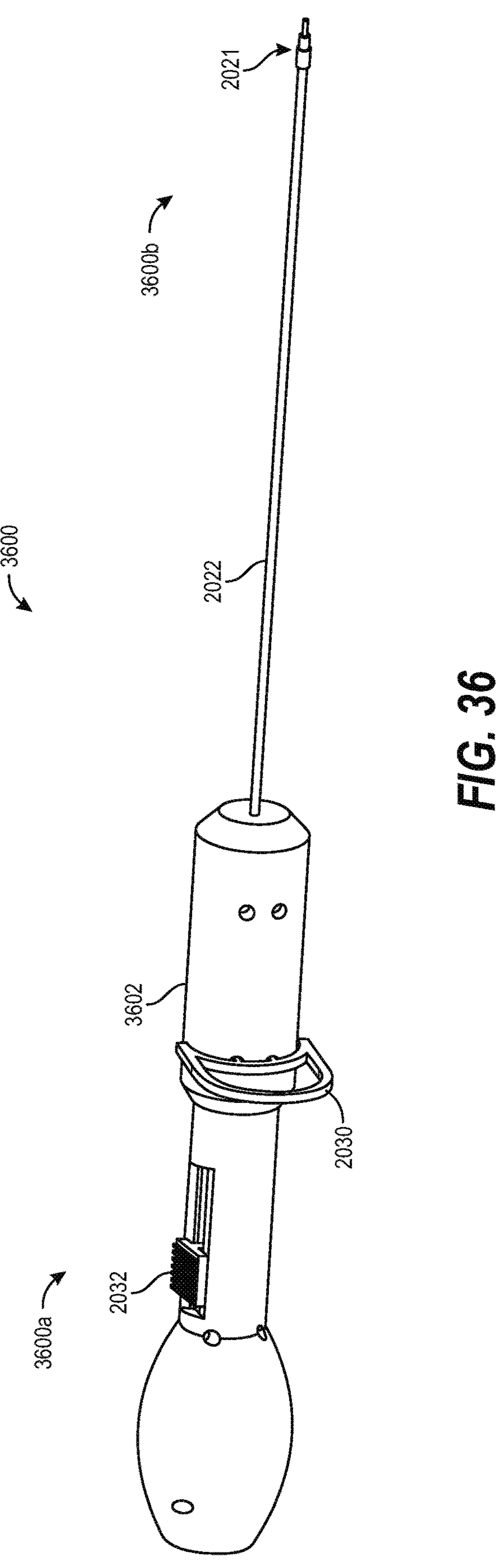
FIG. 36 shows a finishing device configured in accordance with embodiments of the present technology.

FIG. 36 illustrates a finishing device 3600 configured in accordance with several embodiments of the present technology. The finishing device 3600 is configured for use with the treatment devices 100 of the present technology to cut and/or lock the suture 114 once the annulus has been reshaped into a desired geometry. The finishing device 3600 can comprise a proximal portion 3600*a* and a distal portion 3600*b*. The finishing device 3600 can comprise a handle 3602 at the proximal portion 3600*a*, a finishing element 2021 at the distal portion 3600*b*, and an elongate shaft 2022 extending therebetween. The elongate shaft 2022 can be configured to be slidably positioned over the proximal tails of the suture 114, through the coupler 129 (FIG. 1) on the handle 101 of the treatment device 100, and through the elongated shaft 120 to the distal assembly 103. In some embodiments, the elongate shaft 2022 is configured to extend through the lumen of the elongate structure 105. In certain embodiments, the elongate shaft 202 extends through a separate lumen in the elongate shaft 120.

Figures 37A, 37B, 37C, 37D:
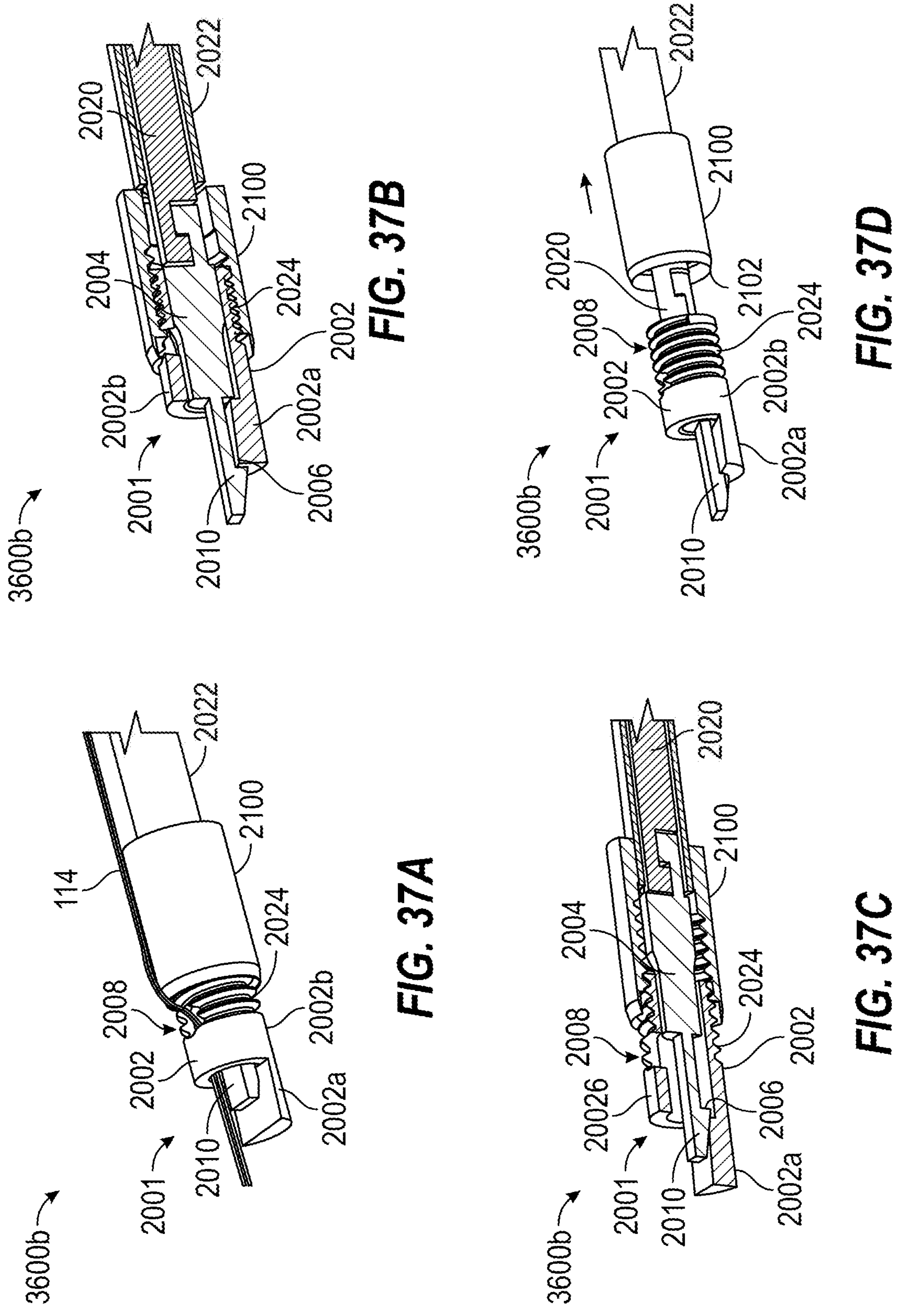
FIGS. 37A-37D show a distal portion of the finishing device of FIG. 36 in different positions in accordance with embodiments of the present technology.

The finishing element 2021 can be configured to lock a desired length of the suture 114 at the annulus and/or can be configured to cut the suture 114. FIGS. 37A and 37B are enlarged perspective and cross-sectional views, respectively, of the finishing element 2021 of the finishing device 3600. The finishing element 2021 can comprise a locking assembly 2001 configured to be coupled to a proximal portion of an anchor (such as any of the anchors of the present technology) and configured to fix the suture 114 in place relative to the corresponding anchor. The locking assembly 2001 is movable between an unlocked configuration (FIGS. 37A and 37B), and a locked configuration (shown in FIG. 37C). In some embodiments the locking assembly 2001 is indirectly coupled to the anchor, for example via a separate component.

The locking assembly 2001 can comprise a base 2002 and a plug 2004 that extends through a lumen of the base 2002. The base 2002 can comprise a tubular body portion 2002*b* and a locking portion 2002*a* extending distally from the body portion 2002*b*. The locking portion 2002*a* can be comprise a ramp that increases in height in a distal direction (away from the body portion 2002*b*). The body portion 2002*b* can have an opening 2008 in its sidewall that is configured to receive a suture 114 therethrough. The body portion 2002*b* can also be threaded along all or a portion of its outer surface.

The plug 2004 can comprise an elongated member having a distal portion 2010 configured to engage a locking portion 2002*a* of the base 2002 and a proximal portion (not labeled) configured to be coupled to an elongate member 2020 that extends proximally to the handle 3602. The distal portion 2010 can have a proximally-facing lip 2006. As the operator pushes the plug 2004 distally (via elongate member 2020), the distal portion 2010 slides distally up the ramp of the locking portion 2002*a* of the base 2002. When the lip 2006 moves distally beyond the distal edge of the ramp, the lip 2006 abuts a distal-facing end surface of the ramp, thereby preventing proximal movement of the plug 2004 relative to the base 2002, as shown in FIG. 37C. With the plug 2004 in this forward position, the suture (not shown) is sandwiched between an intermediate portion 2004*b* of the plug 2004 and an inner surface of the body portion 2002*b*. The intermediate portion of the plug 2004 can be round (or other cross-sectional shapes) and has a cross-sectional dimension sized such that the intermediate portion cannot advance up the ramp of the locking portion 2002*a* of the base 2002, therefore also preventing the plug 2004 from continuing to move distally.

Still referring to FIG. 37C, to cut the suture 114 (not shown), a cutter 2100 with a sharp distal edge 2102 can be advanced over the base 2002 to wedge the portion of the suture extending through the opening 2008 in the base 2002 between the base 2002 and the distal edge 2102 of the cutter 2100. In some embodiments the cutter 2100 is advanced distally by rotating the cutter 2100 over the base 200, which can cut the suture via a shearing force. In such embodiments, an outer surface of at least a proximal portion of the base 2002 of the locking member 2000 can be threaded (such as threads 2024), and an inner surface of the cutter 2100 can have complementary threading. In some embodiments, the cutter 2100 can be advanced distally without rotation of the cutter 2100. For example, the cutter 2100 can be advanced to cut the suture at the portion extending out of the opening 2008. In any case, a proximal end of the cutter 2100 can be coupled to the elongate shaft 2022 that extends back to the handle 3602 for rotational and/or axial control of the cutter 2100. Movement of an actuator 2032 (e.g., a knob, a slider, etc.) at the handle 3602 can translate and rotate the elongate shaft 2022, thereby rotating and advancing the cutter 2100. The elongate shaft 2022 can be a polymer tube, a metal tube (e.g., nitinol, stainless steel, etc.) and may or may not be laser cut. After the suture has been cut, the cutter 2100 can be pulled proximally to expose the connection between the elongate member 2020 and the plug 2004/locking element 2001. This allows the elongate member 2020 and plug 2004 to decouple, thereby allowing the device 3600 to be withdrawn and leaving locking element 2001 behind at the treatment site.

Figure 38:
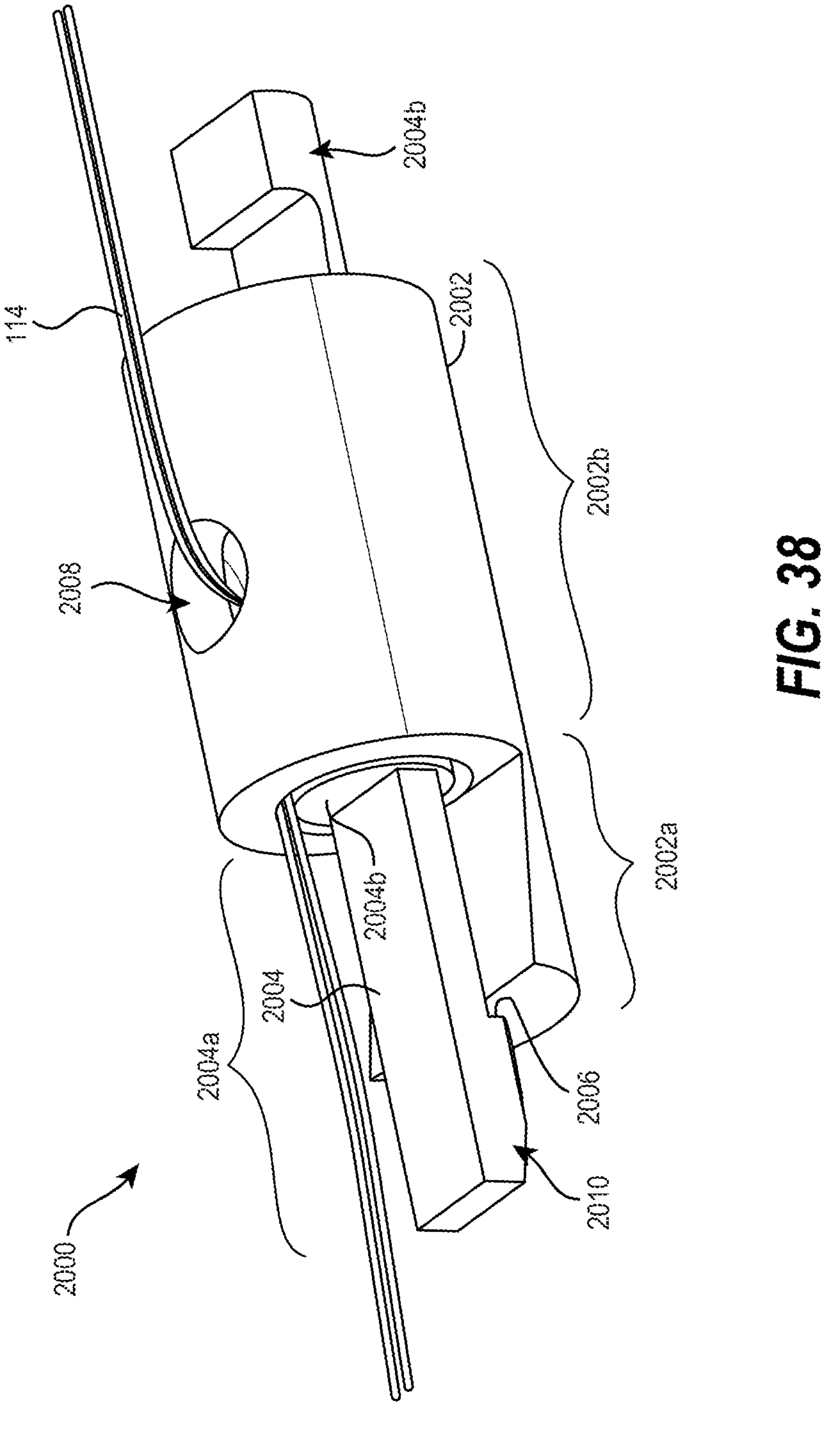
FIGS. 38 and 39 show a distal portion of a finishing device in different states of use and configured in accordance with several embodiments of the present technology.

FIG. 38 depicts a locking member 2000 for use with the treatment systems of the present technology. The locking member 2000 can be coupled to a proximal portion of an anchor (such as any of the anchors of the present technology) and is configured to fix the suture in place relative to the corresponding anchor. The locking member 2000 is movable between an unlocked configuration (not shown), and a locked configuration (shown in FIG. 38). In some embodiments the locking member 2000 is indirectly coupled to the anchor, for example via a separate component.

The locking member 2000 can comprise a tubular base 2002 and a plug 2004 that extends through a lumen of the base 2002. The base 2002 can comprise a body portion 2002*b* and a locking portion 2002*a* extending distally from the body portion 2002*b*. The locking portion 2002*a* can be comprise a ramp that increases in height in a distal direction (away from the body portion 2002*b*). The body portion 2002*b* can have an opening 2008 in its sidewall. A suture can extend distally through the opening 2008 into a lumen of the body portion then out through a distal opening of the body portion 2002*b*.

The plug 2004 can comprise an elongated member having a distal portion 2004*a*, an intermediate portion 2004*b*, and a proximal portion 2004*c*. The distal portion 2004*a* comprises an engagement portion 2010 at its distal end that has a proximally-facing lip 2006. As the physician pushes the plug 2004 distally, the engagement portion 2010 slides distally up the ramp of the locking portion 2002*a* of the base 2002. When the lip 2006 moves distally beyond the distal edge of the ramp, the lip 2006 abuts a distal-facing end surface of the ramp, thereby preventing proximal movement of the plug 2004 relative to the base 2002. With the plug 2004 in this forward position, the suture is sandwiched between the intermediate portion 2004*b* of the plug 2004 and an inner surface of the base 2002. The intermediate portion 2004*b* of the plug 2004 can be round (or other cross-sectional shapes) and has a cross-sectional dimension sized such that the intermediate portion 2004 cannot advance up the ramp of the locking portion 2002*a* of the base 2002, therefore also preventing the plug 2004 from continuing to move distally. The proximal portion 2004*c* of the plug 2004 is configured to be detachably coupled to a portion of the delivery system (such as the distal portion of an arm).

Figure 39:
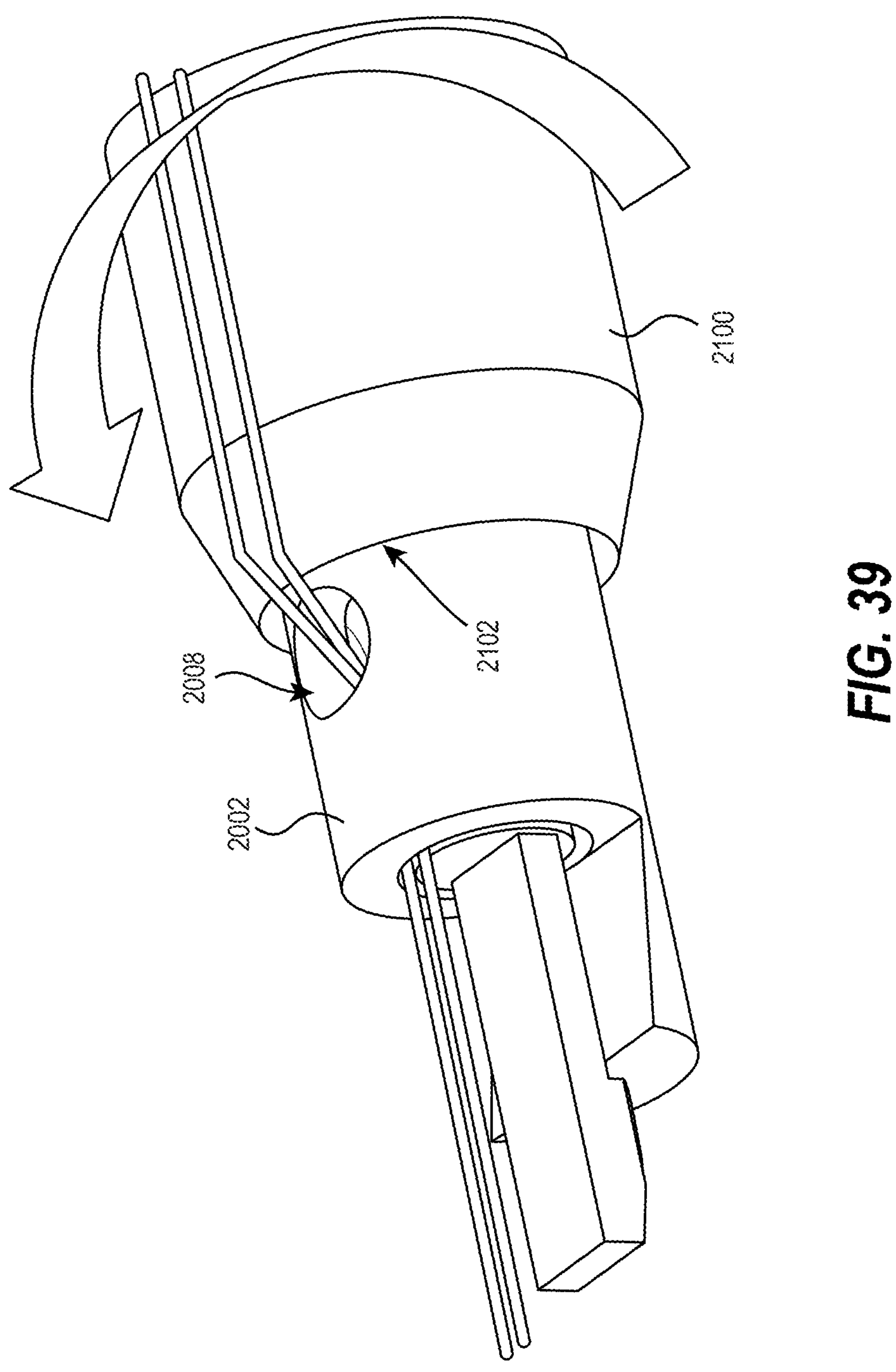

As shown in FIG. 39, to cut the suture a cutter 2100 with a sharp distal edge 2102 can be advanced over the base 2002 to wedge the portion of the suture extending through the opening 2008 in the base 2002 between the base 2002 and the distal edge 2102 of the cutter 2100. In some embodiments the cutter 2100 is advanced distally by rotating the cutter 2100 (as shown in FIG. 39), which can cut the suture via a shearing force. In such embodiments, an outer surface of at least a proximal portion of the base 2002 of the locking member 2000 can be threaded, and an inner surface of the cutter 2100 can have complementary threads. In some embodiments, the cutter 2100 can be advanced distally without rotation of the cutter 2100. For example, the cutter 2100 can be advanced to cut the suture at the portion extending out of the opening 2008. In any case, a proximal end of the cutter can be coupled to an elongated tube that extends back to the handle for rotational and/or axial control of the cutter 2100. would be attached to a tube that goes into the handle and into a knob. The elongated tube can be a polymer tube, a metal tube (e.g., nitinol, stainless steel, etc.) and may or may not be laser cut.

In any of the embodiments disclosed herein, the cutter can be a separate catheter configured tracked over the lock catheter to the location along the suture for cutting.

Many pacemaker leads typically sit around the tricuspid annulus. Existing annular repair device often times disturb the pacemaker lead when trying to place a ring around the annulus of the valve. The design of the present technology advantageously includes a break in the suture loop with two suture portions 114*b* extending proximally through the center of the elongate shaft 120. These portions can be placed between the pacemaker lead without causing any disturbances to the lead.

In some embodiments, the device comprises one or more radiopaque markers disposed at the distal end portion of the elongate shaft 120, the ends of each anchor assembly, and/or the arms so the operator can see where the elongate shaft 120 is as it is being tracked into the patient and where each arm is prior to implantation of the anchors into the tissue. Moreover, with radiopaque markers on the ends of the anchor assemblies, the physician can see where each arm is relative to the heart wall. The two arms on the ends where the suture goes back up to the center of the shaft can have a different marker (e.g., two marker bands, a thicker band, etc.) so the physician can carefully rotate the elongate shaft 120 by rotating the handle 101 such that these two ends can be placed around an existing pacemaker lead.

In some embodiments, physicians can premeasure the valve diameter of the patient (using regular imaging techniques). Because the spacing of the coupler engaging elements on the arms is known, the handle 101 can have markings corresponding to the diameter of area circumscribed by the arms 102 when the coupler 106 is at a given level of coupler engaging elements. The physician can then advance the slider on the handle 101 to a certain point on the handle 101 that is pre-marked. Each pre-marked spot on the handle 101 would correlate to the coupler 106 going down to the next coupler engagement element in the arms. Once the arms are pulled together down to a suitable size, the procedure can continue with the physician being able to control each arm to deploy the corresponding anchors into the tissue. Once all of the anchors are deployed, the physician can then advance the coupler 106 further to bring the arms to a final diameter and/or area.

Another advantage of having multiple arms is that in a situation where the valve is slanted (i.e., in a plane that is angled relative to the approach of the device) and the elongate shaft 120 is coming straight down towards the valve, a physician can make one or more arms shorter (by rotating the arm such that the coupler engaging elements on the arms are not aligned with the arm engaging elements in the coupler and pull backward) and extending the other arms (pushing forward on the arms) to create a slanted implant to treat that slanted valve.

Some devices need to be perpendicular to the valve to be used. The distal assemblies of the present technology can approach the valve perpendicular to the plane of the valve but still treat a slanted valve. With the additional ability to deflect or steer the distal end of the shaft, the devices of the present technology can treat more valves (size, position, and shape) than any other device both commercially available and ones being developed.

Any of the embodiments disclosed herein may further include an imaging element. The imaging element may comprise an elongated member having a distal portion configured to extend proximate the heart valve annulus. The distal portion may have one or more sensors (such as one or more ultrasound transducers, optical elements, etc.) to obtain data at the treatment site that can be manipulated to provide a visual aid to the physician during delivery and implantation of the device. For example, the sensor may capture one or more images of the position of the device relative to the heart valve annulus. The devices and systems of the present technology may further be configured to center the imaging catheter with respect to the implant.

In some embodiments, the imaging element comprises one or more ultrasound transducers. For example, the distal portion of the imaging element may comprise longitudinally disposed and circumferentially disposed ultrasound transducers. The imaging element may be an intravascular ultrasound catheter (IVUS) or an intravascular echocardiography (ICE) catheter. In any case, the imaging element may be contained within and advanced down a central lumen of the delivery catheter. In some embodiments, by rotating the imaging element around the inside of the valve annulus, the relative position of the device and of any valve leaflets will be seen for accurate positioning of the anchors around and above the valve annulus.

In some embodiments, the imaging element is contained within and advanced down an offset, non-central lumen of the elongated shaft 120. In this manner, the imaging element would not interfere with the device, its attachments or other features, and the driver components. In some embodiments, the imaging element may be located and steered to the side of the annulus to image, allowing for less rotation to more quickly view the anchor points of the device. An offset lumen could exit more proximally with regard to the distal end of the elongated shaft 120. This more proximal exit would reduce the overall profile or diameter of the distal end of the delivery catheter. In addition, this more proximal exit port would enable a view of the valve annulus from above. The offset lumen could also be compressible allowing for an even smaller profile until the imaging element is advanced through the offset lumen.

The imaging element may be integrated into the same delivery system as the device, or may be otherwise introduced secondarily through another entry site, such as through the aortic valve, and placed near or inside the implant for imaging and placement of the anchors.

In some embodiments, software or electronic controls can be effective to cycle through the radial cross sectional images around the valve annulus perimeter, relieving the need to physically move, via rotation, translation or deflection, the imaging element. A larger circumferential transducer array could also be placed distal of the annulus to not interfere with space limitations of the delivery catheter, further decreasing the profile of the delivery catheter. In some embodiments, the transducers of the imaging element could generate a three dimensional image of the annulus. The operator could then more readily see the relative alignment of the annulus, valve leaflets and the implant.

In several examples of use, the device 100 can be advanced across the septum separating the upper chambers of the heart. The imaging element is advanced to a position above a valve annulus of the heart, for example, the mitral valve annulus, the tricuspid annulus, the aortic annulus, etc. The device can be expelled from the distal end of the elongate shaft above and proximate to the annulus. A series of radial images can be taken to properly position the anchors for insertion into the annular tissue. For example, an ICE catheter can be advanced through the lumen of the elongate shaft 120 and/or elongate structure 105 and positioned to capture a circumferential image to confirm that all anchors are appropriately placed and anchored in the annular tissue above the leaflets. If one or more anchors are not positioned or anchored properly, they can be rotationally retracted, repositioned and re-anchored prior to removal of the arms and rest of the device. It should also be understood that treatment of the tricuspid valve could involve insertion of the device for access through the jugular vein whereby the device is then advanced down the superior vena cava and into the right atrium proximate and above the tricuspid valve annulus. In some embodiments, the device 100 can be advanced through the femoral artery to the inferior vena cava and into the right atrium to treat the tricuspid valve.

CONCLUSION

Although many of the embodiments are described above with respect to systems, devices, and methods for reshaping a mitral valve annulus, the technology is applicable to other applications and/or other approaches, such as reshaping an aortic valve annulus, the tricuspid valve annulus, or any modification of any valve located at or within the heart or elsewhere. Depending on the valve for treatment, the device can have any number of arms. For example, a device for treating the mitral valve may utilize six arms, while a device for treating the larger triscuspid valve may require eight. Moreover, other embodiments in addition to those described herein are within the scope of the technology. Additionally, several other embodiments of the technology can have different configurations, components, or procedures than those described herein. A person of ordinary skill in the art, therefore, will accordingly understand that the technology can have other embodiments with additional elements, or the technology can have other embodiments without several of the features shown and described above with reference to FIGS. 1-39.

The descriptions of embodiments of the technology are not intended to be exhaustive or to limit the technology to the precise form disclosed above. Where the context permits, singular or plural terms may also include the plural or singular term, respectively. Although specific embodiments of, and examples for, the technology are described above for illustrative purposes, various equivalent modifications are possible within the scope of the technology, as those skilled in the relevant art will recognize. For example, while steps are presented in a given order, alternative embodiments may perform steps in a different order. The various embodiments described herein may also be combined to provide further embodiments.

Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Additionally, the term "comprising" is used throughout to mean including at least the recited feature(s) such that any greater number of the same feature and/or additional types of other features are not precluded. It will also be appreciated that specific embodiments have been described herein for purposes of illustration, but that various modifications may be made without deviating from the technology. Further, while advantages associated with certain embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

As used herein, the terms "generally," "substantially," "about," and similar terms are used as terms of approximation and not as terms of degree, and are intended to account for the inherent variations in measured or calculated values that would be recognized by those of ordinary skill in the art.

We claim:

1. A device for treating a native valve annulus, the device comprising:

a plurality of arms, each having a proximal portion and a distal portion, wherein the plurality of arms are configured to translate independently of one another;

a coupler coupled to the plurality of arms and configured to move relative to the plurality of arms; and a plurality of anchors, each carried by the distal portion of one of the plurality of arms and configured to engage tissue at or proximate the native valve annulus, wherein, when the device is in a deployed configuration such that the plurality of arms extend axially and radially away from the coupler, movement of the coupler relative to the plurality of arms decreases a circumferential distance between at least some of the plurality of anchors.

2. The device of claim 1, wherein the coupler is configured to translate and/or rotate relative to the plurality of arms.

3. The device of claim 1, wherein the plurality of arms are configured to rotate independently of one another.

4. The device of claim 1, wherein each of the plurality of arms includes one or more locking elements, and wherein movement of the coupler relative to the plurality of arms causes the coupler to engage at least some of the locking elements on at least some of the plurality of arms, thereby fixing an axial position of each of the plurality of arms relative to the other plurality of arms and/or the coupler.

5. The device of claim 1, wherein, when the plurality of arms are in a deployed configuration, movement of the coupler relative to the plurality of arms decreases an angle between adjacent arms of the plurality of arms.

6. The device of claim 1, wherein the plurality of arms comprises at least three arms.

7. The device of claim 1, wherein each of the plurality of anchors is detachably coupled to one of the plurality of arms such that, upon completion of treatment, the coupler and the plurality of arms are removed from the patient while the plurality of anchors are left implanted at the native valve annulus.

8. The device of claim 1, wherein each of the plurality of anchors is attached to a single arm.

9. The device of claim 1, further comprising a suture coupled to the plurality of anchors.

10. The device of claim 1, wherein some or all of the plurality of arms comprise at least one of a tube, a solid rod, or a ribbon.

11. The device of claim 1, wherein the native valve annulus is a cardiac valve annulus, and wherein the device is configured to be percutaneously delivered proximate to and above the cardiac valve annulus such that the plurality of anchors are implanted in the annular cardiac tissue just above the plane of the valve orifice.

12. A device for treating a native valve annulus, the device comprising:

a plurality of arms, each having a proximal portion and a distal portion, wherein the arms are configured to translate relative to one another;

a coupler coupled to the plurality of arms and configured to move relative to the plurality of arms, wherein each of the plurality of arms has a first length proximal to the coupler and a second length distal to the coupler, and wherein the distal portions of each of the plurality of arms are not coupled to another one of the plurality of arms such that the second lengths of the plurality of arms are cantilevered from the coupler; and a plurality of anchors, each carried by the distal portion of one of the plurality of arms and configured to engage tissue at or proximate the native valve annulus, wherein, when the device is in a deployed configuration such that the second lengths of the plurality of arms extend axially and radially away from the coupler, movement of the coupler relative to the plurality of arms decreases a circumferential distance between at least some of the plurality of anchors.

13. The device of claim 12, wherein the plurality of arms are configured to rotate independently of one another.

14. The device of claim 12, wherein the coupler is configured to translate and/or rotate relative to the plurality of arms.

15. The device of claim 12, wherein each of the plurality of arms includes one or more locking elements, and wherein movement of the coupler relative to the plurality of arms causes the coupler to engage at least some of the locking elements on at least some of the plurality of arms, thereby fixing an axial position of each of the plurality of arms relative to the other arms of the plurality of arms and/or the coupler.

16. The device of claim 12, wherein, when the plurality of arms are in a deployed configuration, movement of the coupler relative to the plurality of arms decreases an angle between adjacent arms of the plurality of arms.

17. The device of claim 12, wherein the plurality of arms comprises at least three arms.

18. The device of claim 12, wherein each of the plurality of anchors is detachably coupled to one of the plurality of arms such that, upon completion of treatment, the coupler and the plurality of arms are removed from the patient while the plurality of anchors are left implanted at the native valve annulus.

19. The device of claim 12, wherein each of the plurality of anchors is attached to a single arm.

20. The device of claim 12, wherein the native valve annulus is a cardiac valve annulus, and wherein the device is configured to be percutaneously delivered proximate to and above the cardiac valve annulus such that the plurality of anchors are implanted in the annular cardiac tissue just above the plane of the valve orifice.

* * * * *